United States Patent [19]

Minamida et al.

[11] Patent Number: 5,256,679

[45] Date of Patent: Oct. 26, 1993

[54] SUBSTITUTED GUANIDINE DERIVATIVES, THEIR PREPARATION AND USE

[75] Inventors: Isao Minamida; Yasuyuki Kando; Hitoshi Ishizuka, all of Ibaraki; Tetsuo Okauchi, Osaka; Hideki Uneme, Ibaraki, all of Japan

[73] Assignee: Takeda Chemical Industries, Ltd., Osaka, Japan

[21] Appl. No.: 745,245

[22] Filed: Aug. 14, 1991

[30] Foreign Application Priority Data

| Aug. 17, 1990 | [JP] | Japan | 2-217356 |
| Aug. 20, 1990 | [JP] | Japan | 2-219628 |
| Oct. 15, 1990 | [JP] | Japan | 2-276628 |
| Mar. 1, 1991 | [JP] | Japan | 3-036108 |
| May 16, 1991 | [JP] | Japan | 3-111987 |

[51] Int. Cl.$^5$ .............. C07D 277/28; C07D 277/30; C07D 213/26; A01N 43/78
[52] U.S. Cl. .................. 514/357; 514/365; 546/330; 546/332; 548/204; 548/205
[58] Field of Search .......... 548/204, 205; 546/330, 546/337; 514/357, 505

[56] References Cited

U.S. PATENT DOCUMENTS

| 4,567,188 | 1/1986 | Niemers et al. | 514/332 |
| 5,084,467 | 1/1992 | Shiokawa | 514/357 |

FOREIGN PATENT DOCUMENTS

| 0302833 | 1/1990 | European Pat. Off. |
| 0375907 | 7/1990 | European Pat. Off. |
| 0376279 | 7/1990 | European Pat. Off. |
| 0383091 | 8/1990 | European Pat. Off. |

*Primary Examiner*—Robert Gerstl
*Attorney, Agent, or Firm*—Wegner, Cantor, Mueller & Player

[57] ABSTRACT

Novel substituted nitroguanidine derivatives and salts thereof having the following formula:

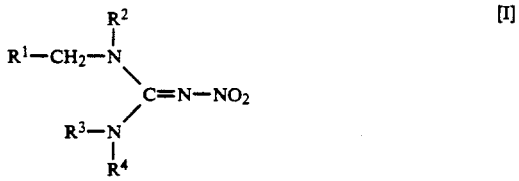

wherein $R^1$ is a substituted or unsubstituted heterocyclic group; $R^2$ is a group attached through a sulfur atom, a group attached through a phosphorus atom, cyano, —CO—OR$^6$ wherein $R^6$ is a substituted or unsubstituted hydrocarbon group or a substituted or unsubstituted heterocyclic group, or —CO—NR$^7$R$^8$ wherein $R^7$ and $R^8$, which are the same or different, are each independently hydrogen, a substituted or unsubstituted hydrocarbon group or a substituted or unsubstituted heterocyclic group, or $R^7$ and $R^8$, taken together with the nitrogen atom to which they are attached are a cyclic amino group; $R^3$ is hydrogen, a substituted or unsubstituted hydrocarbon group (except for one substituted with an oxo group at the binding site), a group attached through a sulfur atom, a group attached through a phosphorus atom, cyano, —CO—R$^9$ wherein $R^9$ is hydrogen, a substituted or unsubstituted hydrocarbon group or a substituted or unsubstituted heterocyclic group, —CO—OR$^{10}$ wherein $R^{10}$ is a substituted or unsubstituted hydrocarbon group or a substituted or unsubstituted heterocyclic group, or —CO—NR$^{11}$R$^{12}$ wherein $R^{11}$ and $R^{12}$, which are the same or different, are each independently hydrogen, a substituted or unsubstituted hydrocarbon group or a substituted or unsubstituted heterocyclic group, or $R^{11}$ and $R^{12}$, taken together with the nitrogen atom to which they are attached are a cyclic amino group; and $R^4$ is hydrogen or a lower alkyl group; which have unexpectedly potent pesticidal activity and very low toxicity.

42 Claims, No Drawings

SUBSTITUTED GUANIDINE DERIVATIVES, THEIR PREPARATION AND USE

FIELD OF THE INVENTION

The present invention relates to novel substituted nitroguanidine derivatives and salts thereof, which are useful as pesticidal agents, their preparation and pesticidal compositions containing the same.

BACKGROUND OF THE INVENTION

Various synthetic compounds having inhibitory actions against harmful pests and the like have been employed as insecticides. Most of such agents are classified into organic phosphate esters, carbamic esters, organic chlorine-containing compounds and pyrethroid compounds. It has been well known that frequent use of such limited compounds causes harmful effects, for example increase of insecticide-resistant pests, etc. and thus such problems raise public discussions in various places. Among the above-mentioned insecticides, some compounds exert potent insecticidal actions but possess high toxicities to human beings, domestic animals and fish, in some cases show toxic influence on natural enemies of pests, and a high residual property in soil or the like. Accordingly, they are still unsatisfactory in practical uses.

Guanidine derivatives and salts thereof have been disclosed as insecticides, for example, in European Patent Application Laid Open Nos. 0,375,907 A1 and 0,376,279 A2; however, there are not described any nitroguanidine derivatives wherein the guanidine nitrogen is substituted with a cyano group or a group attached thereto through a sulfur or phosphorus atom or a carbonyl group except for formyl and acetyl.

SUMMARY OF THE INVENTION

Thus, it is the object of the present invention to provide a new class of pesticides which have potent insecticidal activity and excellent controlling effect on pests and are of low toxicity to human beings, domestic animals, fish and natural enemies of pests and safe. Further objects of the present invention are to provide chemical processes and intermediates for the preparation of such pesticides and their salts and derivatives and to provide agricultural and horticultural compositions comprising such pesticides and methods for controlling harmful living beings, i.e. pests, insects, acarids, mites, etc. by using such pesticides and compositions thereof.

The present invention provides novel substituted nitroguanidine compounds having the following formula:

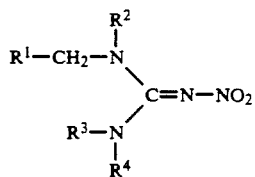

wherein $R^1$ is a substituted or unsubstituted heterocyclic group; $R^2$ is a group attached through a sulfur atom, a group attached through a phosphorus atom, cyano, —CO—OR$^6$ wherein $R^6$ is a substituted or unsubstituted hydrocarbon group or a substituted or unsubstituted heterocyclic group, or —CO—NR$^7$R$^8$ wherein $R^7$ and $R^8$, which are the same or different, are each independently hydrogen, a substituted or unsubstituted hydrocarbon group or a substituted or unsubstituted heterocyclic group, or $R^7$ and $R^8$, taken together with the nitrogen atom to which they are attached are a cyclic amino group; $R^3$ is hydrogen, a substituted or unsubstituted hydrocarbon group (except for one substituted with an oxo group at the binding site), a group attached through a sulfur atom, a group attached through a phosphorus atom, cyano, —CO—R$^9$ wherein $R^9$ is a substituted or unsubstituted hydrocarbon group or a substituted or unsubstituted heterocyclic group, —CO—OR$^{10}$ wherein $R^{10}$ is a substituted or unsubstituted hydrocarbon group or a substituted or unsubstituted heterocyclic group, or —CO—NR$^{11}$R$^{12}$ wherein $R^{11}$ and $R^{12}$, which are the same or different, are each independently hydrogen, a substituted or unsubstituted hydrocarbon group or a substituted or unsubstituted heterocyclic group, or $R^{11}$ and $R^{12}$, taken together with the nitrogen atom to which they are attached are a cyclic amino group; and $R^4$ is hydrogen or a lower alkyl group; and salts thereof, which have unexpectedly potent pesticidal activity and very low toxicity.

DETAILED DESCRIPTION OF THE INVENTION

The present invention relates to
(1) a substituted nitroguanidine compound of the formula [I] or a salt thereof,

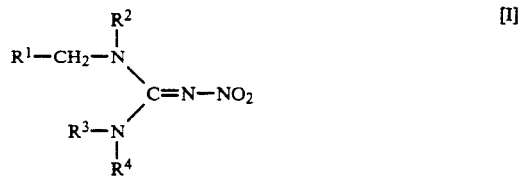

wherein $R^1$ is a substituted or unsubstituted heterocyclic group; $R^2$ is a group attached through a sulfur atom, a group attached through a phosphorus atom, cyano, —CO—OR$^6$ wherein $R^6$ is a substituted or unsubstituted hydrocarbon group or a substituted or unsubstituted heterocyclic group, or —CO—NR$^7$R$^8$ wherein $R^7$ and $R^8$, which are the same or different, are each independently hydrogen, a substituted or unsubstituted hydrocarbon group or a substituted or unsubstituted heterocyclic group, or $R^7$ and $R^8$, taken together with the nitrogen atom to which they are attached are a cyclic amino group; $R^3$ is hydrogen, a substituted or unsubstituted hydrocarbon group (except for one substituted with an oxo group at the binding site), a group attached through a sulfur atom, a group attached through a phosphorus atom, cyano, —CO—R$^9$ wherein $R^9$ is hydrogen, a substituted or unsubstituted hydrocarbon group or a substituted or unsubstituted heterocyclic group, —CO—OR$^{10}$ wherein $R^{10}$ is a substituted or unsubstituted hydrocarbon group or a substituted or unsubstituted heterocyclic group, or —CO—NR$^{11}$R$^{12}$ wherein $R^{11}$ and $R^{12}$, which are the same or different, are each independently hydrogen, a substituted or unsubstituted hydrocarbon group or a substituted or unsubstituted heterocyclic group, or $R^{11}$ and $R^{12}$, taken together with the nitrogen atom to which they are attached are a cyclic amino group; and $R^4$ is hydrogen or a lower alkyl group;

(2) a pest control composition containing an effective amount of the substituted nitroguanidine compound of the formula [I]or the salt thereof, in admixture with a agrochemically acceptable carrier, vehicle, diluent or excipient;

(3) a process for preparing a substituted nitroguanidine compound of the formula [I$^a$]:

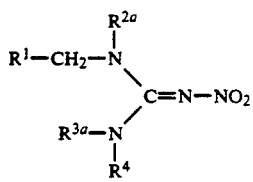

wherein R$^1$ has the same meaning as defined above; R$^{2a}$ has the same meaning as above-defined for R$^2$; R$^3$, is hydrogen or a substituted or unsubstituted hydrocarbon group except for one substituted with an oxo group at the binding site; and R$^4$ has the same meaning as defined above; or a salt thereof, which comprises reacting a compound of the formula [II]:

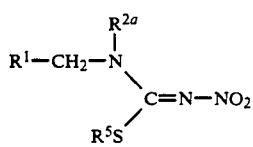

wherein R$^1$ and R$^{2a}$ have the same meanings as defined above and R$^5$ is a substituted or unsubstituted hydrocarbon group or a substituted or unsubstituted acyl group, or a salt thereof, with a compound of the formula [III]:

 [III]

wherein R$^{3a}$ and R$^4$ have the same meanings as defined above, or a salt thereof, (4) a process for preparing a substituted nitroguanidine compound of the formula [I]or a salt thereof, which comprises reacting a compound of the formula [IV]:

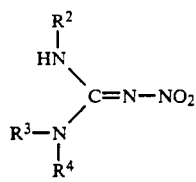

wherein each has the same meaning as defined above, or a salt thereof, with a compound of the formula [V]:

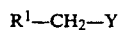 [V]

wherein R$^1$ has the same meaning as defined above and Y is a leaving group, (5) a process for preparing a substituted nitroguanidine compound of the formula [I$^b$]:

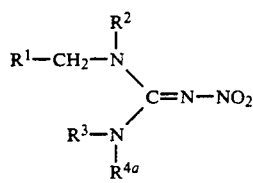

wherein R$^1$, R$^2$ and R$^3$ have the same meanings as defined above and R$^{4a}$ is a lower alkyl group, or a salt thereof, which comprises reacting a compound of the formula [I$^c$]:

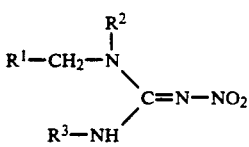

wherein each group has the same meaning as defined above, or a salt thereof, with a compound of the formula [VI]:

 [VI]

wherein each group has the same meaning as defined above, (6) a process for preparing a substituted nitroguanidine compound of the formula [I$^d$]:

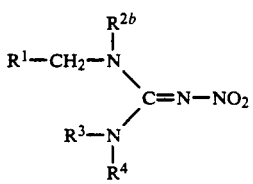

wherein R$^1$, R$^3$ and R$^4$ have the same meanings as defined above and R$^{2b}$ has the same meaning as above-defined for R$^2$, or a salt thereof, which comprises reacting a compound of the formula [I$^e$]:

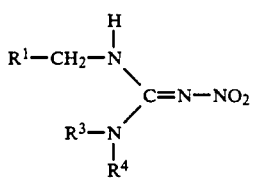

wherein each group has the same meaning as defined above, or a salt thereof, with a compound of the formula [VII]:

 [VII]

wherein each group has the same meaning as defined above, (7) a process for preparing a substituted nitroguanidine compound of the formula [I$^f$]:

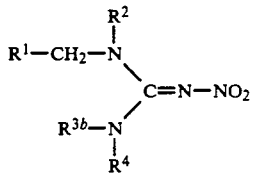

wherein R$^1$, R$^2$ and R$^4$ have the same meanings as defined above and R$^{3b}$ is a substituted or unsubstituted hydrocarbon group (except for one substituted with an oxo group at the binding site), a group attached through a sulfur atom, a group attached through a phosphorus atom, cyano, —CO—R$^9$ wherein R$^9$ is hydrogen, a substituted or unsubstituted hydrocarbon group or a substituted or unsubstituted heterocyclic group, —CO—OR$^{10}$ wherein R$^{10}$ is a substituted or unsubstituted hydrocarbon group or a substituted or unsubstituted heterocyclic group, or —CO—NR$^{11}$R$^{12}$ wherein R$^{11}$ and R$^{12}$, which are the same or different, are each independently hydrogen, a substituted or unsubstituted hydrocarbon group or a substituted or unsubstituted heterocyclic group, or R$^{11}$ and R$^{12}$, taken together with the nitrogen atom to which they are attached are a cyclic amino group, or a salt thereof, which comprises reacting a compound of the formula [I$^g$]:

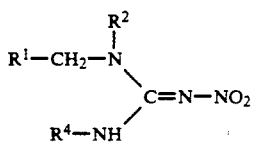  [I$^g$]

wherein each group has the same meaning as defined above, or a salt thereof, with a compound of the formula [VIII]:

R$^{3b}$—Y  [VIII]

wherein each group has the same meaning as defined above, (8) a process for preparing a substituted nitroguanidine compound of the formula [I] or a salt thereof, which comprises reacting a compound of the formula [IX]:

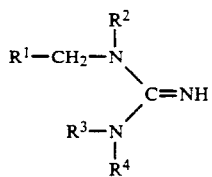  [IX]

wherein each group has the same meaning as defined above, or a salt thereof, with a nitrating reagent, (9) a process for preparing a substituted nitroguanidine compound of the formula [I$^h$]:

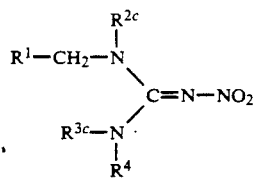  [I$^h$]

wherein R$^1$ and R$^4$ have the same meanings as defined above; and R$^{2c}$ is a group attached through a sulfur atom, a group attached through a phosphorus atom, cyano, —CO—OR$^6$ wherein R$^6$ is a substituted or unsubstituted hydrocarbon group or a substituted or unsubstituted heterocyclic group, or —CO—NR$^7$R$^{8,}$ wherein R$^7$ and R$^8$, which are the same or different, are each independently hydrogen, a substituted or unsubstituted hydrocarbon group or a substituted or unsubstituted heterocyclic group, or R$^7$ and R$^8$, taken together with the nitrogen atom to which they are attached are a cyclic amino group; R$^{3c}$ is hydrogen, a substituted or unsubstituted hydrocarbon group (except for one substituted with an oxo group at the binding site), a group attached through a sulfur atom, a group attached through a phosphorus atom, cyano, —CO—R$^9$ wherein R$^9$ is hydrogen, a substituted or unsubstituted hydrocarbon group or a substituted or unsubstituted heterocyclic group, —CO—OR$^{10}$ wherein R$^{10}$ is a substituted or unsubstituted hydrocarbon group or a substituted or unsubstituted heterocyclic group, or —CO—NR$^{11}$R$^{12}$ wherein R$^{11}$ and R$^{12}$, which are the same or different, are each independently hydrogen, a substituted or unsubstituted hydrocarbon group or a substituted or unsubstituted heterocyclic group, or R$^{11}$ and R$^{12}$, taken together with the nitrogen atom to which they are attached are a cyclic amino group, provided that at least one of R$^{2c}$ and R$^{3c}$ is the substituted or unsubstituted aminocarbonyl group as defined above, or a salt thereof, which comprises reacting a compound of the formula [I$^i$]:

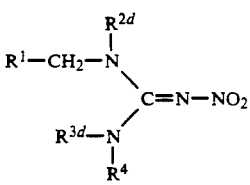  [I$^i$]

wherein R$^1$ and R$^4$ have the same meanings as defined above; and R$^{2d}$ is a group attached through a sulfur atom, a group attached through a phosphorus atom, cyano, —CO—OR$^6$ wherein R$^6$ is a substituted or unsubstituted hydrocarbon group or a substituted or unsubstituted heterocyclic group, —CO—NR$^7$R$^8$ wherein R$^7$ and R$^8$, which are the same or different, are each independently hydrogen, a substituted or unsubstituted hydrocarbon group or a substituted or unsubstituted heterocyclic group, or R$^7$ and R$^{8,}$ taken together with the nitrogen atom to which they are attached are a cyclic amino group, or a reactive carboxyl group; R$^{3d}$ is hydrogen, a substituted or unsubstituted hydrocarbon group (except for one substituted with an oxo group at the binding site), a group attached through a sulfur atom, a group attached through a phosphorus atom, cyano, —CO—R$^9$ wherein R$^9$ is hydrogen, a substituted or unsubstituted hydrocarbon group or a substituted or unsubstituted heterocyclic group, —CO—OR- wherein R$^{10}$ is a substituted or unsubstituted hydrocarbon group or a substituted or unsubstituted heterocyclic group, or —CO—NR$^{11}$R$^{12}$ wherein R$^{11}$ and R$^{12}$, which are the same or different, are each independently hydrogen, a substituted or unsubstituted hydrocarbon group or a substituted or unsubstituted heterocyclic group, or R$^{11}$ and R$^{12}$, taken together with the nitrogen atom to which they are attached are a cyclic amino group, or a reactive ester which is —CO—OR$^6$ or —CO—OR$^{10}$, respectively, or a salt thereof, with a compound of the formula:

R$^7$R$^8$NH  [X]

or R$^{11}$R$^{12}$NH  [XI]

wherein each group has the same meaning as defined above, and

(10) a method for controlling a pest which comprises applying an effective amount of the substituted nitroguanidine compound of the formula [I] or the salt thereof to prevent said pest.

An important group of compounds according to the present invention are the compounds of the formula [I']

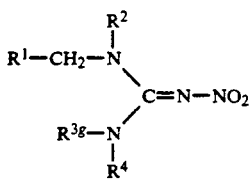

wherein $R^1$ is a substituted or unsubstituted heterocyclic group; $R^2$ is a group attached through a sulfur atom, a group attached through a phosphorus atom, cyano, —CO—OR$^6$ wherein $R^6$ is a substituted or unsubstituted hydrocarbon group or a substituted or unsubstituted heterocyclic group, or —CO—NR$^7$R$^8$ wherein $R^7$ and $R^8$, which are the same or different, are each independently hydrogen, a substituted or unsubstituted hydrocarbon group or a substituted or unsubstituted heterocyclic group, or $R^7$ and $R^8$, taken together with the nitrogen atom to which they are attached are a cyclic amino group; $R^{3g}$ is hydrogen or a substituted or unsubstituted hydrocarbon group (except for one substituted with an oxo group at the binding site); and $R^4$ is hydrogen or a lower alkyl group; and salts thereof. Among the compound [I'], a compound the formula [I'j]:

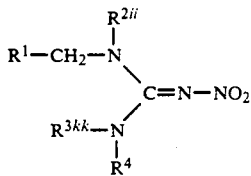

wherein $R^1$ and $R^4$ has the same meaning as defined above; $R^{2ii}$ is $C_{2-7}$ alkoxycarbonyl group such as or methoxycarbonyl, ethoxycarbonyl and the like; $R^{3kk}$ is hydrogen or $C_{1-4}$ alkyl group such as methyl, ethyl, propyl and the like; or a salt thereof, is preferred. The compound [I'j] can be prepared by the same process as for the compound [I$^a$], which comprises reacting a compound of the formula:

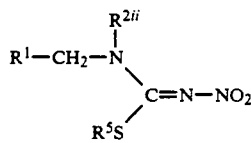

wherein $R^1$, $R^{2ii}$ and $R^5$ have the same meanings as defined above, or salt thereof, with a compound of the formula:

wherein $R^{3kk}$ and $R^4$ have the same meanings as defined above, or a salt thereof.

Another important group of compounds according to the present invention are the compounds of the formula [I$^k$]:

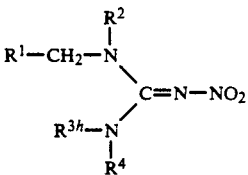

wherein $R^1$ is a substituted or unsubstituted heterocyclic group; $R^2$ is a group attached through a sulfur atom, a group attached through a phosphorus atom, cyano, —CO—OR$^6$ wherein $R^6$ is a substituted or unsubstituted hydrocarbon group or a substituted or unsubstituted heterocyclic group, or —CO—NR$^7$R$^8$ wherein $R^7$ and $R^8$, which are the same or different, are each independently hydrogen, a substituted or unsubstituted hydrocarbon group or a substituted or unsubstituted heterocyclic group, or $R^7$ and $R^8$, taken together with the nitrogen atom to which they are attached are a cyclic amino group; $R^{3h}$ is hydrogen; and $R^4$ is hydrogen or a lower alkyl group; and salts thereof.

Still another important group of compounds according to the present invention are the compounds of the formula [I$^l$]:

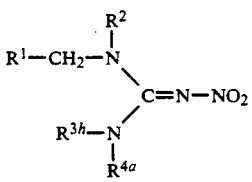

wherein $R^1$ is a substituted or unsubstituted heterocyclic group; $R^2$ is a group attached through a sulfur atom, a group attached through a phosphorus atom, cyano, —CO—OR$^6$ wherein $R^6$ is a substituted or unsubstituted hydrocarbon group or a substituted or unsubstituted heterocyclic group, or —CO—NR$^7$R$^8$ wherein $R^7$ and $R^8$, which are the same or different, are each independently hydrogen, a substituted or unsubstituted hydrocarbon group or a substituted or unsubstituted heterocyclic group, or $R^7$ and $R^8$, taken together with the nitrogen atom to which they are attached are a cyclic amino group; $R^{3h}$ is hydrogen; and $R^{4a}$ is a lower alkyl group; and salts thereof.

In the foregoing formulas, $R^1$ represents a substituted or unsubstituted heterocyclic group. The heterocyclic group for $R^1$ is a cyclic group containing only the same heteroatoms or a cyclic group containing two or more different heteroatoms, e.g. a heterocyclic group having a single or fused ring with 5 to 8 ring members in each ring and having from one to five heteroatoms in each ring independently selected from oxygen, nitrogen and sulfur. Examples of the heterocyclic group for $R^1$ include 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(I,2,4-thiadiazolyl), 1,3,4-thiadiazolyl, 4- or 5-(I,2,3-thiadiazolyl), 1,2,5-thiadiazolyl, 1,2,3-triazolyl, 1,2,4-triazolyl, IH- or 2H-tetrazolyl, N-oxide of 2-, 3- or 4-pyridyl, 2-, 4- or 5-pyrimidinyl, N-oxide of 2-, 4- or 5-pyrimidinyl, 3- or 4-pyridazinyl, pyrazinyl, N-oxide of 3- or 4-pyridazinyl, benzofuryl, benzothiazolyl, benzoxazolyl, triazinyl, oxotriazinyl, tetrazolo[1,5-b]pyridazinyl, triazolo[4,5-b]pyridazinyl, oxoimidazolyl, dioxotriazinyl, pyrrolidinyl, piperidyl, pyranyl, thiopyranyl, 1,4-oxazinyl, morpholinyl, 1,4-thiazinyl, 1,3-thiazinyl, piperazinyl, benzimidazolyl, quinolyl, isoquinolyl, einnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl, and phenoxazinyl. Specific examples of suitable heterocyclic groups include five- or six-membered nitrogen-containing heterocyclic groups such as 2-, 3- or 4-pyridyl and 2-, 4- or 5-thiazolyl. These heterocyclic groups may have 1 to 5 (preferably 1) substituent groups which are the same or different. Examples of such substituent groups include but are not limited to $C_{1-15}$ alkyl groups such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, and pentadecyl; $C_{3-10}$ cycloalkyl groups such as cyclopropyl, cyclobutyl, cyclopentyl, and cyclohexyl; $C_{2-10}$ alkenyl groups such as vinyl, allyl, 2-methylallyl, 2-butenyl, 3-butenyl, and 3-octenyl; $C_{2-10}$ alkynyl groups such as ethynyl, 2-propynyl, and 2-hexynyl; $C_{3-10}$ cycloalkenyl groups such as cyclopropenyl, cyclopentenyl, and cyclohexenyl; $C_{6-10}$ aryl groups such as phenyl and naphthyl; $C_{7-10}$ aralkyl groups including phenylalkyl groups such as benzyl, and phenethyl; nitro; hydroxyl; mereapto; oxo; thioxo; cyano; carbamoyl; carboxyl; $C_{1-4}$ alkoxycarbonyl groups such as methoxycarbonyl and ethoxycarbonyl; sulfo (—$SO_3H$); halogens such as fluorine, chlorine, bromine and iodine; $C_{1-4}$ alkoxy groups such as methoxy, ethoxy, propoxy, isopropoxy, butoxy, isobutoxy, s-butoxy, and t-butoxy; $C_{6-10}$ aryloxy groups such as phenoxy; $C_{1-4}$ alkylthio groups such as methylthio, ethylthio, n-propylthio, isopropylthio, n-butylthio, and t-butylthio; $C_{6-10}$ arylthio groups such as phenylthio; $C_{1-4}$ alkylsulfinyl groups such as methylsulfinyl and ethylsulfinyl; $C_{6-10}$ arylsulfinyl groups such as phenylsulfinyl; $C_{1-4}$ alkylsulfonyl groups such as methylsulfonyl and ethylsulfonyl; $C_{6-10}$ arylsulfonyl groups such as phenylsulfonyl; amino; $C_{2-6}$ acylamino groups including alkanoylamino groups such as acetylamino and propionylamino; mono- or di-$C_{1-4}$ alkylamino groups such as methylamino, ethylamino, n-propylamino, isopropylamino, n-butylamino, dimethylamino, and diethylamino; $C_{3-6}$ cycloalkylamino groups such as cyclohexylamino; $C_{6-10}$ arylamino groups such as aniline; $C_{2-4}$ acyl including alkanoyl groups such as acetyl; $C_{6-10}$ arylcarbonyl such as benzoyl; as well as five- to six-membered heterocyclic groups each containing 1 to 4 heteroatoms selected from oxygen, sulfur and nitrogen, such as 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-,4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidinyl, 3- or 4-pyridazinyl, quinolyl, isoquinolyl, and indolyl.

In the case where the substituent group is, for example, $C_{6-10}$ aryl, $C_{7-10}$ aralkyl, $C_{3-10}$ cycloalkyl, $C_{3-10}$ cycloalkenyl, $C_{6-10}$ aryloxy, $C_{6-10}$ arylthio, $C_{6-10}$ arylsulfinyl, $C_{6-10}$ arylsulfonyl, $C_{6-10}$ arylamino, or heterocyclic group, it may be additionally substituted with one to five substituent groups selected from the group consisting of halogen as above-mentioned; hydroxyl; $C_{1-4}$ alkyl such as methyl, ethyl, propyl, isopropyl, butyl, isobutyl, s-butyl, and t-butyl; $C_{2-4}$ alkenyl such as vinyl, allyl, and 2-methylallyl; $C_{2-4}$ alkynyl such as ethynyl and 2-propynyl; $C_{6-10}$ aryl as above-mentioned; $C_{1-4}$ alkoxy as above-mentioned; phenoxy; $C_{1-4}$ alkylthio as above-mentioned; and phenylthio.

In the case where the substituent group is, for example, $C_{1-15}$ alkyl, $C_{2-10}$ alkenyl, $C_{2-10}$ alkynyl, $C_{1-4}$ alkoxy, $C_{1-4}$ alkylthio, $C_{1-4}$ alkylsulfinyl, $C_{1-4}$ alkylsulfonyl, amino, mono-or di-$C_{1-4}$ alkylamino, $C_{3-6}$ cycloalkylamino, or $C_{6-10}$ arylamino, it may be additionally substituted with one to five substituent groups selected from the group consisting of halogen as above-mentioned; hydroxyl; $C_{1-4}$ alkoxy as above-mentioned; and $C_{1-4}$ alkylthio as above-mentioned.

Preferred examples of $R^1$ are five- or six-membered nitrogen-containing heterocyclic groups such as pyridyl and thiazolyl which may be substituted with one or two halogens.

The hydrocarbon group in the "substituted or unsubstituted hydrocarbon group" for $R^3$, $R^{3a}$, $R^{3b}$, $R^{3c}$, $R^{3d}$, $R^{3g}$, $R^5$, $R^6$, $R^7$, $R^8$, $R^9$, $R^{10}$, $R^{11}$ and $R^{12}$ includes $C_{1-15}$ alkyl groups, $C_{3-10}$ cycloalkyl groups, $C_{2-10}$ alkenyl groups, $C_{2-10}$ alkynyl groups, $C_{3-10}$ cycloalkenyl groups, $C_{6-10}$ aryl groups and $C_{7-10}$ aralkyl groups as mentioned in the substituent group for $R^1$.

The substituent group on the "substituted or unsubstituted hydrocarbon group" for $R^3$, $R^{3a}$, $R^{3b}$, $R^{3c}$, $R_{3d}$, $R^{3g}$, $R^5$, $R^6$, $R^7$, $R^8$, $R^9$, $R^{10}$, $R^{11}$ and $R^{12}$ includes those mentioned in the substituent group on the heterocyclic group for $R^1$.

The heterocyclic group in the "substituted or unsubstituted heterocyclic group" for $R^6$, $R^7$, $R^8$, $R^9$, $R^{10}$, $R^{11}$ and $R^{12}$ includes those groups mentioned herein for $R^1$.

The substituent group on the "substituted or unsubstituted heterocyclic group" for $R^6$, $R^7$, $R^8$, $R^9$, $R^{10}$, $R^{11}$ and $R^{12}$ includes those mentioned in the substituent group on the heterocyclic group for $R^1$.

The groups attached through a sulfur atom for $R^2$, $R^{2a}$, $R^{2b}$, $R^{2c}$, $R^{2d}$, $R^{2e}$, $R^{2f}$, $R^3$, $R^{3b}$, $R^{3c}$, and $R^{3d}$ include, for example, —$S(O)_n$—$R^{13}$ wherein n is an integer of 0, 1 or 2 and $R^{13}$ is a hydrocarbon group or a heterocyclic group. The hydrocarbon groups for $R^{13}$ include, for example, those mentioned herein for $R^1$. The heterocyclic groups for $R^{13}$ include, for example, those mentioned herein for $R^1$. Such hydrocarbon and heterocyclic groups for $R^{13}$ may have from one to five substituent groups as above-mentioned herein for $R^1$.

The groups attached through a phosphorus atom for $R^2$, $R^{2a}$, $R^{2b}$, $R^{2c}$, $R^{2d}$, $R^{2e}$, $R^{2f}$, $R^3$, $R^{3b}$, $R^{3c}$, and $R^{3d}$ include, for example, —$P(=O)R^{14}R^{15}$ wherein $R^{14}$ and $R^{15}$, which are the same or different, are hydroxyl, a hydrocarbon or heterocyclic group attached through an oxgen atom, or a hydrocarbon or heterocyclic group. The hydrocarbon groups for $R^{14}$ and $R^{15}$ include, for example, those as mentioned herein for $R^1$. The heterocyclic groups for $R^{14}$ and $R^{15}$ include, for example, those mentioned herein for $R^1$. Such hydrocarbon and heterocyclic groups for $R^{14}$ and $R^{15}$ may have from one to five substituent groups as above-mentioned herein for $R^1$.

The cyclic amino groups which are formed from $R^7$ and $R^8$ taken together with the nitrogen to which they are attached, include, for example, aziridino, azetidino, pyrrolidino, piperazino, piperidino, morpholino, thiomorpholino, and the like. Such cyclic amino groups may be substituted with one to four substituents, for example, $C_{1-4}$ alkyl groups such as methyl and ethyl.

The cyclic amino groups which are formed from $R^{11}$ and $R^{12}$ taken together with the nitrogen to which they are attached, include, for example, aziridino, azetidino, pyrrolidino, piperazino, piperidino, morpholino, thiomorpholino, and the like. Such cyclic amino groups may be substituted with one to four substituents, for example, $C_{1-4}$ alkyl groups such as methyl and ethyl.

Preferred examples for $R^2$ include, for example, $C_{2-7}$ alkoxycarbonyl groups such as methoxycarbonyl, ethoxycarbonyl, n-propoxycarbonyl and n-hexyloxycarbonyl; $C_{7-12}$ aryloxycarbonyl groups such as phenoxycarbonyl; $C_{8-13}$ aralkyloxycarbonyl such as benzyloxycarbonyl; $C_{2-7}$ alkylaminocarbonyl groups such as methylaminocarbonyl, ethylaminocarbonyl, propylaminocarbonyl and n-hexylaminocarbonyl; di-$C_{1-4}$ alkylaminocarbonyl groups such as dimethylaminocarbonyl, diethylaminocarbonyl and ethylmethylaminocarbonyl; saturated cyclic aminocarbonyl groups such as morpholinocarbonyl, pyrrolidinocarbonyl and piperidinocarbonyl; and $C_{1-4}$ alkylsulfonyl groups such as methanesulfonyl and ethanesulfonyl. Particularly preferred examples of the substituent groups for $R^2$ are methoxycarbonyl, ethoxycarbonyl, n-propoxycarbonyl, or isopropoxycarbonyl.

Preferred examples for $R^3$ include, for example, hydrogen, $C_{1-4}$ alkyl such as methyl, ethyl, propyl, isopropyl, butyl, isobutyl, s-butyl, and t-butyl; $C_{1-7}$ acyl groups such as formyl, acetyl, propionyl, n-butyryl, i-butyryl and heptanoyl; $C_{7-12}$ arylcarbonyl groups such as benzoyl; $C_{2-7}$ alkoxycarbonyl groups such as methoxycarbonyl, ethoxycarbonyl, n-propoxycarbonyl and n-hexyloxycarbonyl; $C_{7-12}$ aryloxycarbonyl groups such as phenoxycarbonyl; $C_{8-13}$ aralkyloxycarbonyl such as benzyloxycarbonyl; $C_{2-7}$ alkylaminocarbonyl groups such as methylaminocarbonyl, ethylaminocarbonyl, propylaminocarbonyl and n-hexylaminocarbonyl; di-$C_{1-4}$ alkylaminocarbonyl groups such as dimethylaminocarbonyl, diethylaminocarbonyl and ethylmethylaminocarbonyl; saturated cyclic aminocarbonyl groups such as morpholinocarbonyl, pyrrolidinocarbonyl and piperidinocarbonyl; and $C_{1-4}$ alkylsulfonyl groups such as methanesulfonyl and ethanesulfonyl. Particularly preferred examples of the substituent groups for $R^3$ are hydrogen or $C_{1-4}$ alkyl such as methyl, ethyl, propyl, isopropyl, butyl, isobutyl, s-butyl, and t-butyl. The most preferred example of the substituent group for $R^3$ is hydrogen.

The lower alkyl groups for $R^4$ and $R^{4a}$ include, for example, $C_{1-4}$ alkyl groups such as methyl, ethyl, n-propyl, i-propyl, n-butyl, i-butyl, s-butyl, t-butyl and the like. Preferred examples of $R^4$ are, for example, hydrogen and $C_{1-2}$ alkyl groups such as methyl and ethyl.

$R^5$ represents a substituted or unsubstituted hydrocarbon, or substituted or unsubstituted acyl group. Examples of such hydrocarbon groups include, for example, $C_{1-10}$ alkyl groups and $C_{7-12}$ aralkyl groups as above-mentioned herein. Examples of such acyl groups include, for example, $C_{1-10}$ acyl groups as above-mentioned herein. Such hydrocarbon and acyl groups for $R^5$ may have from one to five substituent groups as above-mentioned herein for $R^1$. Preferred examples for $R^5$ are, for example, $C_{1-4}$ alkyl groups such as methyl, ethyl, propyl and butyl, which may be substituted with carboxyl, sulfo or the like, $C_{7-12}$ aralkyl groups such as benzyl, which may be substituted with carboxyl, sulfo or the like, etc.

Concrete examples for $R^2$ and $R^3$ are already mentioned hereinbefore. Among these, when the subject compound is an aminocarbonyl derivative, the group for —CO—$OR^6$ or —CO—$OR^{10}$ is one capable of easily leaving as —$OR^6$ or —$OR^{10}$, respectively. Specific examples for $R^6$ and $R^{10}$ are 1-halogeno-$C_{1-4}$ alkyl groups such as 1-chloroethyl and the like, polyhalogenophenyl groups such as 2,4,5-trichlorophenyl, 2,3,4,5,6-pentachlorophenyl and the like, preferably.

The leaving groups for Y include, for example, halogens such as fluorine, chlorine, bromine and iodine; $C_{1-4}$ alkylsulfonyloxy groups optionally substituted with one to three halogens (e.g. Cl, Br, F, etc.), such as methanesulfonyloxy, ethanesulfonyloxy, butanesulfonyloxy and trifluoromethanesulfonyloxy; and $C_{6-10}$ arylsulfonyloxy groups optionally substituted with one to four halogens (e.g. Cl, Br, F, etc.), such as benzenesulfonyloxy, p-toluenesulfonyloxy, p-bromobenzenesulfonyloxy and mesitylenesulfonyloxy. Specific examples of the leaving groups for Y are, for example, halogens such as chlorine and bromine, $C_{1-4}$ alkylsulfonyloxy groups optionally substituted with one to three halogens, for example, such as methanesulfonyloxy, and trifluoromethanesulfonyloxy; and $C_{6-10}$ arylsulfonyloxy groups such as benzenesulfonyloxy and p-toluenesulfonyloxy.

Among the compounds represented by the above formula (I), a preferred embodiment of the invention is a compound of the formula:

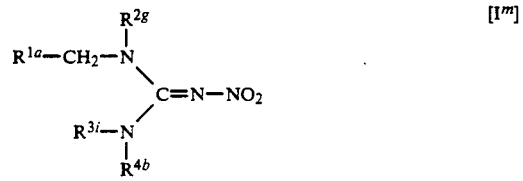

[I^m]

wherein $R^{1a}$ is pyridyl, halogenopyridyl, thiazolyl, or halogenothiazolyl; $R^{2g}$ is $C_{2-7}$ alkoxycarbonyl; $R^{3i}$ is hydrogen, or $C_{1-4}$ alkyl such as methyl, ethyl and propyl, or $C_{7-12}$ arylcarbonyl; and $R^{4b}$ is hydrogen or $C_{1-4}$ alkyl such as methyl, ethyl and propyl; or a salt thereof. Specific examples of the substituent groups for $R^{1a}$ are, for example, halogenopyridyl such as 6-chloro-3-pyridyl, 6-bromo-3-pyridyl and 5-bromo-3-pyridyl, or halogenothiazolyl such as 2-chloro-5-thiazolyl and 2-bromo-5-thiazolyl.

Among the compounds represented by the above formula (I), a more preferred embodiment of the invention is a compound of the formula:

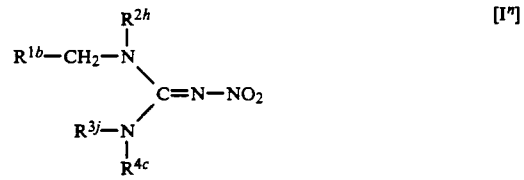

[I^n]

wherein $R^{1b}$ is pyridyl, halogenopyridyl, thiazolyl, or halogenothiazolyl; $R^{2b}$ is $C_{2-7}$ alkoxycarbonyl such as methoxycarbonyl and ethoxycarbonyl; $R^{3j}$ is hydrogen; and $R^{4b}$ is methyl or ethyl; or a salt thereof. In the compounds [I^n], specific examples of the substituent groups for $R^{1b}$ are, for example, halogenopyridyl such as 6-chloro-3-pyridyl, 6-bromo-3-pyridyl and 5-bromo-3-pyridyl, or halogenothiazolyl such as 2-chloro-5-thiazolyl and 2-bromo-5-thiazolyl.

The salts of the guanidine derivatives [I], [I$^a$], [I$^b$], [I$^c$], [I$^d$], [I$^e$], [I$^f$], [I$^g$], [I$^h$], [I$^i$], [I$^j$], [I$^k$], [I$^l$], [I$^m$] and [I$^n$] are preferably agrochemically acceptable salts. Examples of the salts include salts with inorganic acids such as hydrochloric acid, hydrobromic acid, hydriodic acid, phosphoric acid, sulfuric acid, and perchloric acid, as well as organic acids such as formic acid, acetic acid, tartaric acid, malic acid, citric acid, oxalic acid, succinic acid, benzoic acid, picric acid, and p-toluenesulfonic acid.

The substituted nitroguanidine derivatives [I] or salts thereof can be employed as insecticide in any application form suitable for conventional agricultural chemicals. For example, one or more species of these compounds [I] and salts thereof can be dissolved or dispersed in a suitable liquid vehicle, or admixed with or adsorbed on a suitable solid carrier, according to purposes of use, to form a suitable formulation or preparation such as an emulsifiable concentrate, oil, water soluble solid, hydrate, wettable powder, dust, flowable dust, granule, tablet, liquid, spray, aerosol, fumigant, painting, paste or ointment. These formulations can be prepared by any conventional method known per se. For example, they may contain, if necessary, an emulsifier, suspending agent, spreader, penetrant, wetting agent, thickener, mucilage, stabilizer, etc.

The proportion of the active constituents in a pesticide can vary according to intended uses. For example, an appropriate range is about 10 to 90 wt % in the case of an emulsifiable concentrate and wettable powder, about 0.1 to 10 wt % in the case of oil and dust, about 1 to 20 wt % in the case of granules, etc. The concentration of active ingredients may be changed according to intended uses. The emulsifiable concentrate and wettable powder are sprinkled after being diluted or extended with water or the like (e.g. 100 to 100,000-fold).

Suitable examples of the liquid vehicle or carrier (solvent) include water, alcohols (e.g. methyl alcohol, ethyl alcohol, n-propyl alcohol, isopropyl alcohol, ethylene glycol, etc.), ketones (e.g. acetone, methyl ethyl ketone, etc.), ethers (e.g. dioxane, tetrahydrofuran, ethylene glycol monomethyl ether, diethylene glycol monomethyl ether, propylene glycol monomethyl ether, etc.), aliphatic hydrocarbons (e.g. kerosene, fuel oil, machine oil, etc.), aromatic hydrocarbons (e.g. benzene, toluene, xylene, solvent naphtha, methylnaphthalene, etc.), halogenated hydrocarbons (e.g. dicholoromethane, chloroform, carbon tetrachloride, etc.), acid amides (e.g. dimethylformamide, dimethylacetamide, etc.), esters (e.g. ethyl acetate, butyl acetate, fatty acid glycerol ester, etc.), and nitriles (e.g. acetonitrile, propionitrile, etc.). These solvents may be used individually or in a suitable mixed form of two or more ingredients in a suitable ratio.

Examples of the solid carrier (diluent/extender) include vegetable powders (e.g. soybean meal, tobacco powder, wheat flour, sawdust, etc.), mineral powders (e.g. clays such as kaolin, bentonite, terra alba, talcs such as talcum powder and agalmatolite powder, and silicas such as diatomaceous earth and mica powder), alumina, sulfur powder, and active carbon. These solid carriers may be used individually or in a suitable mixed form of two or more ingredients in a suitable ratio.

Examples of ointment bases include polyethylene glycol, pectin, polyhydric alcohol esters of higher fatty acids such as monostearic acid glycerol ester, cellulose derivatives such as methyl cellulose, sodium alginate, bentonite, higher alcohols, polyhydric alcohols such as glycerin, vaseline, white petrolatum, liquid paraffin, lard, various vegetable oils, lanolin, dehydrated lanolin, hardened oil, and resins. These ointment bases may be used alone, in a suitable mixed form of two or more ingredients or in admixture with various surfactants as mentioned hereinbelow.

The surfactants which can be employed as said emulsifier, spreading agent, penetrating agent or dispersing agent include various soaps and nonionic or anionic surface active agents such as polyoxyethylene alkyl aryl ethers [e.g. Noigen TM and E . A 142 TM, Dai-ichi Kogyo Seiyaku K.K.; Nonal TM, Toho Kagaku K.K.], alkyl sulfates [e.g. Emal 10 TM and Emal 40 TM, Kao K.K.], alkyl sulfonates [e.g. Neogen TM and Neogen T TM, Dai-ichi Kogyo Seiyaku K.K.; Neopellex, Kao K.K.], polyethylene glycol ethers [e.g. Nonipol 85 TM, Nonipol 100 TM and Nonipol 160 TM, Sanyo Kasei K.K.] and polyhydric alcohol esters [e.g. Tween 20 TM and Tween 80 TM, Kao K.K.I.

The substituted nitroguanidine derivative [I] or salt thereof can be used, as the case may be, in combination with other insecticides (e.g. pyrethroid insecticides, organophosphorus insecticides, carbamate insecticides, natural insecticides), acaricides, miticides, nematocides, herbicides, plant hormones, plant growth regulators, fungicides (e.g. copper fungicides, organochlorine fungicides, organosulfur fungicides, phenolic fungicides), synergists, attractants, repellents, pigments, fertilizers and manures.

Representative examples of said insecticide, acaricide, miticide and fungicide which may be employed in admixture with the compound of the present invention include propoxur, isoprocarb, BPMC, xylylearb, metolearb, XMC, ethiofenearb, carbaryl, pirimicarb, bendiocarb, carbofuran, furathiocarb, carbosulfan, aminosulfulan, methomyl, fenthion, fenitrothion, propaphos, cyanophos, prothiofos, sulprofos, profenofos, EPN, cyanofenphos, acephate, oxydeprofos, disulfoton, thiometon, phenthoate, malathion, dimethoate, vamidothion, mecarbam, trichlorphon, naled, dichlorvos, chlorofenvinphos, tetrachlorvinphos, monocrotophos, phosalone, dialifos, chlorpyrifos-methyl, chlorpyrifos, pirimiphos-methyl, diazinon, etrimfos, pyridaphenthion, quinalphos, isoxathion, methidathion, salithion, cyfluthrin, permethrin, cypermethrin, deltamethrin, eyhalothrin, fenpropathrin, fenvalerate, flucythrinate, flubalinate, cartap, thiocyclam, buprofezin, difulbenzuron, ethofenprox, fthalide, validamycin A, mepronil, flutolanil, Monguard TM, pencycuron, edifenphos, isoprothiolane, tricyclazole, probenazole, kasugamycin, IBP, bensultap. pyraclophos, ferimzon, imidaeloprid, nitenpyram, sigma-cypermethrin, fipronil, silanophane, novaluron, hydroprene, flufenprox, fenpyrad or tebufenpyrad, fenoxycarb, fenazaquin, chlorfluazuron, nomolt, hexaflumuron, flufenoxuron, alanyearb, diafenthiuron, clofentezine, fenpropathrin, tralomethrin, methoxadiazone, fluazinam, okimeranolure, chlorthiophos, fortress, levamisol, dienochlor, cloethocarb, cycloprothrin, benfuracarb, isofenphos, avermectin, milbemycin, fenothiocarb, cyromazine, flucycloxuron, butathiofos, fenpyroximate, acrinathrin, benfluthrin, pyridaben, pyriproxyfen, hexythiazox, cycloprothrin, cherrytlure, sulfluramid, diamolure, thiodicarb, fenpropathrin, pyriproxyfen, diafenthiuron, fenarimol, flurprimidol, fluotrimazole, tradimafon, triadimenol, diclobutazol, paclobutazol, diniconazole, uniconazole, triflumizole, propiconazole, flutriafol, flusilazole, penconazole, butiobate, prochloraz, teiapenthenol, EDDP, pyroquilon, chlobenthiazone, zineb, maneb, TPN, captan, captafol, folpet, dichlorfluanid, carboxin, oxycarboxin, pyracarbolid, mebenil, furcarbanil, cyclafuramid, benodanil, granovax, thiabendazole, fuberidazole, benomyl, thiophanate-methyl, cypendazole, carbendazin, dichlozoline, iprodione, vinclozolin, proeymidone, myclozolin, ftalaxyl, metalaxyl, ofrace, benalaxyl, oxadixyl, cyprofuram, tridemorph, fenpropimorph, triforine, triarimol, fenarimol, bitetanol, imazalil, etaconazole, paclobutrazol, phenapronil, triflumizole, viniconazole, ethirimol, dimethirimol, fluoroimide, hymexazol, ethazol, proxychlor, pyrazophos, prothiocarb, aliette, fenpropidin, flapenazole, pyrifenox, diethofenearb, pipanipirim, clozylacon, difenoconazole, dimethomorph, fenpiclonil, thicyofen, bromuconazole, opus, ipconazole, dimetconazole, myclobutanil, myxothiazol, thioimiconazole, zarilamid, metsulfovax, hexaconazole, quinconazole, tecloftalam, tolelofos-methyl, fenpropidin, triclamide, flusulfamide, befran, cyproconazole, tecloftalam, furconazole-cis, fenethanil, dimefluazole, ethyltrianol, tebuconazole, oxolinic acid, and the like.

The substituted nitroguanidine derivative [I] and salts thereof are effective in controlling sanitary or horticultural insect pests and animal/plant parasitic insects, and exhibit potent insecticidal action when contacted directly with insects, for example, by being sprinkled directly over animals and plants with insect pests parasitic thereon. More interesting characteristics of the pesticide of the present invention are that they are highly insecticidal even when they are once absorbed into plants through their root, leaves, or stem and thereafter sucked, gnawed or chewed by insects or contacted with insects. Such properties are advantageous in controlling sucking, gnawing or chewing pests. Furthermore, the compounds [I] and salts thereof are of low side effects on plants and also of low toxicity against fish. Thus, they possess safe and advantageous properties as pest controlling agents in sanitary, horticultural and particularly agricultural fields.

The horticultural and agricultural compositions containing the substituted nitroguanidine derivatives [I] and/or salts thereof are advantageously effective in the control of Hemiptera pests such as, for example, *Eurydema rugosum, Scotinophara lurida, Riptortus clavatus, Stephanitis nashi, Laodelphax striatellus, Nilaparvata lugens, Nephotettix eincticeps, Unaspis yanonensis, Aphis glycines, Lipaphis erysimi, Brevicoryne brassicae,* and *Aphis gossypii*; Lepidoptera pests such as, for example, *Spodoptera litura, Plutella xylostella, Pieris rapae crucivora, Chilo suppressalis, Autographs nigrisigna, Helicoverpa assulta, Pseudaletia separata, Mamestra brassicae, Adoxophyes orana fasciata, Notarcha derogata, Cnaphalocrocis medinalis,* and *Phthorimaea operculella*; Coleoptera pests such as, for example, *Epilachna vigintioctopunctata, Aulacophora femoralis, Phyllotreta striolata, Oulema oryzae,* and *Echinocnemus squameus*; Diptera pests such as, for example, *Musca domestics, Culex pipiens pollens, Tabanus trigonus, Delia antiqua,* and *Delia platura*; Orthoptera pests such as, for example, *Locusts migratoria* and *Gryllotalpa africana*; Blattidae pests such as, for example, *Blattella germanica* and *Periplaneta fuliginosa*; spider mites such as, for example, *Tetranychus urticae, Panonychus citri, Tetranychus kanzawai, Tetranychus cinnabarinus, Panonychus ulmi,* and *Aculops pelekassi*; and Nematoda such as, for example, *Aphelenchoides besseyi.*

The pesticidal composition thus obtained is extremely low in toxicity and is safe and excellent as an agrochemical. It can be used in the same manner as in conventional insecticides and exert superior effects in comparison with conventional products. For example, the pesticide of the present invention can be applied to target pests by treating in nursery pots, sprinkling over stems and leaves of crop, sprinkling directly on insects, treating irrigation water in paddy fields, or soils. The application amount can vary over a wide range, depending on the season, place and method of application, etc. Preferably, the pesticide of the invention is employed, in general, in such a manner that the proportion of active ingredient (substituted nitroguanidine derivative [I] and/or salt thereof) is in the range of 0.3 to 3,000 g, more preferably 50 to 1,000 g, per hectare. In the case where the pesticide of the present invention is in the form of a wettable powder, it may be employed by diluting before use so that the final concentration of active ingredient is in the range of 0.1 to 1,000 ppm, preferably 10 to 500 ppm.

The substituted nitroguanidine derivatives [I] and their salts of the present invention can be prepared by Processes (A) to (G) described below.

In the case where the substituted nitroguanidine derivative [I] is obtained in its free form, it can be converted into the corresponding salt as mentioned above by conventional methods. When the substituted nitroguanidine derivative [I] is obtained in its salt form, it can be converted into the corresponding free form by conventional methods. Also, any substituted nitroguanidine derivative [I] may be in any of free or salt form when it is used as a raw material for preparing another substituted nitroguanidine derivatives [I]. Other raw materials than the substituted nitroguanidine derivative [I] which can form salts can be employed as any of free or salt form. Accordingly, raw materials to be employed and products in the below-mentioned Processes include their respective salts (e.g. salts with the acids as mentioned above in the compound [I]).

(A) The compound [II] or salt thereof is reacted with ammonia, primary or secondary amine or a salt thereof represented by the formula [III] to form the nitroguanidine derivative [I$^a$] according to the present invention. In the reaction, it is especially preferred to use the compound [II] wherein $R^5$ is $C_{1-4}$ alkyl optionally substituted with carboxyl or sulfo such as methyl, carboxymethyl, sulfomethyl and 2-sulfoethyl, or benzyl optionally substituted with carboxyl or sulfo such as 4-carboxybenzyl.

The compound [III] or salt thereof is preferably used in an amount of about 0.8 to 2.0 equivalents per compound [II] or salt thereof but may be used in an amount of about 2.0 to 20 equivalents as far as the reaction is not impeded.

The reaction is usually carried out in a suitable solvent, although it may be performed in the absence of solvent. Examples of such solvent include water; alcohols such as methanol, ethanol, n-propanol and isopropanol; aromatic hydrocarbons such as benzene, toluene and xylene; halogenated hydrocarbons such as dichloromethane and chloroform; saturated hydrocarbons such as hexane, heptane and cyclohexane; ethers such as diethyl ether, tetrahydrofuran (hereinafter abbreviated as THF) and dioxane; ketones such as acetone; nitriles such as acetonitrile; sulfoxides such as dimethyl sulfoxide (hereinafter abbreviated as DMSO); acid amides such as N,N-dimethylformamide (hereinafter abbreviated as DMF); esters such as ethyl acetate; and carboxylic acids such as acetic acid and propionic acid. These solvents may each be used alone or, if necessary, in admixture of two or more kinds in a suitable ratio, for example in the range of 1:1 to 1:10. In the case where the reaction mixture is not homogeneous, the reaction may be carried out in the presence of a phase transfer catalyst such as a quaternary ammonium salt (e.g. triethylbenzylammonium chloride, tri-n-octylmethylammonium chloride, trimethyldecylammonium chloride, or tetramethylammonium bromide), or a crown ether.

The reaction may be accelerated by the addition of a base or metallic salt in an amount of 0.01 to 10 equivalents, preferably 0.1 to 3 equivalents. Examples of such bases include inorganic bases such as sodium hydrogencarbonate, potassium hydrogencarbonate, sodium carbonate, potassium carbonate, sodium hydroxide, potassium hydroxide, calcium hydroxide, phenyl lithium, butyl lithium, sodium hydride, potassium hydride, sodium methoxide, sodium ethoxide, metal sodium, and metal potassium, as well as organic bases such as triethylamine, tributylamine, N,N-dimethylaniline, pyridine, lutidine, collidine, 4-(dimethylamino)pyridine, and DBU (1,8-diazabicyclo[5,4,0]undecene-7). These organic bases per se can also be used as solvents. Examples of the metallic salts include copper salts such as copper chloride, copper bromide, copper acetate, and copper sulfate, as well as mercury salts such as mercury chloride, mercury nitrate and mercury acetate.

In the reaction, the reaction temperature is usually in the range of $-50°$ to $150°$ C., preferably $-20°$ C. to $100°$ C. and the reaction time is usually in the range of 10 minutes to 50 hours, preferably 1 to 20 hours.

(B) The compound [IV] or salt thereof is reacted with the compound [V] or salt thereof to form the nitroguanidine derivative [I] according to the present invention.

Preferred examples of the leaving groups represented by Y in the the compound [V] include, for example, halogens such as chlorine and bromine; $C_{1-4}$ alkylsulfonyloxy groups such as methanesulfonyloxy; $C_{6-10}$ arylsulfonyloxy groups such as p-toluenesulfonyloxy; and $C_{1-4}$ acyl groups optionally substituted with one to three halogens (e.g. Cl, Br, F, etc.), such as acetyloxy and trifluoroacetyloxy.

The compound [V] or salt thereof is preferably used in an amount of about 0.8 to 1.5 equivalents per compound [IV] or salt thereof although a large excess amount may be used as far as the reaction is not impeded.

In order to accelerate the reaction, it may be carried out in the presence of a base. Examples of such bases include those listed in Process (A). The base can be used in an amount of about 0.5 equivalents to a large excess amount per compound [IV], preferably about 0.8 to 1.5 equivalents. The organic base when used as the base can serve as the solvent. In some case, the addition of a catalytic amount (e.g. about 0.003 to 0.05 molar equivalents) of cesium salts such as cesium fluoride, cesium carbonate and cesium acetate) can improve the yield.

The reaction is preferably carried out in a suitable solvent as mentioned in Process (A). In the case where the reaction mixture is not homogeneous, the reaction may be carried out in the presence of a phase transfer catalyst as mentioned in Process (A).

In the reaction, the reaction temperature is usually in the range of $-20°$ to $150°$ C., preferably $0°$ C. to $80°$ C. and the reaction time is usually in the range of 10 minutes to 50 hours, preferably 2 to 20 hours.

(C) The compound [I$^c$] or salt thereof is reacted with the compound [VI] to form the nitroguanidine derivative [I$^b$] according to the present invention. In the reaction, preferred examples of Y and the reaction conditions are the same as those stated in Process (B).

(D) The compound [I$^e$] or salt thereof is reacted with the compound [VII] to form the nitroguanidine derivative [I$^d$] according to the present invention. In the reaction, when $R^{2b}$ is a cyano group, preferred examples of Y and the reaction conditions are the same as those stated in Process (B). When $R^{2b}$ represents a group attached through a sulfur or phosphorus atom, $-CO-OR^6$ wherein $R^6$ is a substituted or unsubstituted hydrocarbon group or a substituted or unsubstituted heterocyclic group, or $-CO-NR^7R^8$ wherein $R^7$ and $R^8$, which are the same or different, are each independently hydrogen, a substituted or unsubstituted hydrocarbon group or a substituted or unsubstituted heterocyclic group, or $R^7$ and $R^8$, taken together with the nitrogen atom to which they are attached are a cyclic amino group, the reaction may be carried out by or according to conventional or known methods. Examples of the reacting agents employed in the alkoxycarbonylation, aryloxycarbonylation, aralkyloxycarbonylation, heterocycloxycarbonylation, and heterocycle-substituted alkoxycarbonylation include, for example, oxycarbonyl halides and carbonate esters containing a group represented by $R^6$. Examples of the reacting agents employed in the sulfenylation, sulfinylation, and sulfonylation include, for example, sulfenyl halides, sulfinyl halides, and sulfonyl halides, and sulfonic acid anhydrides containing a group represented by $R^{13}$. Examples of the reacting agents employed in the phosphorylation include, for example, phosphoryl halides containing groups represented by $R^{14}$ and $R^{15}$.

Preferred examples of the halogens in the above-mentioned reacting halides are bromine and chlorine. The reagent is preferably used in at least a molar equivalent per starting compound, more preferably in an amount of about 1 to 5 molar equivalents. The solvent employed in the reaction is not limited to but includes any as long as it dissolves the compound [I$^e$] and reagent. Preferred examples of the solvents include, for example, dichloromethane, chloroform, dichloroethane, tetrahydrofuran, dioxane, N,N-dimethylformamide, N,N-dimethylacetamide, dimethyl sulfoxide, hexamethylenephosphorotriamide, pyridine, acetonitrile, and the like.

In the reaction, the reaction temperature is usually in the range of $-50°$ to $150°$ C., and the reaction time is usually in the range of about 0.1 to 48 hours. For the purpose of accelerating the reaction or reducing the formation of by-product, the reaction may be performed in the presence of a base. Examples of the bases include, for example, amines such as triethylamine, dimethylaminopyridine, pyridine, N,N-dimethylaniline and N,N-diethylaniline; sodium hydride; potassium hydride; sodium amide; n-butyl lithium; lithium diisopropylethylamide; and the like.

(E) The compound [I$^g$] or salt thereof is reacted with the compound [VIII] to form the nitroguanidine derivative [I$^f$] according to the present invention. In the reaction, when $R^{3b}$ is a substituted or unsubstituted hydrocarbon group or cyano group, preferred examples of Y and the reaction conditions are the same as those stated in Process (B). When $R^{3b}$ represents $-CO-R^9$, $-CO-OR^{10}$, $-CONR^{11}R^{12}$, or a group attached through a sulfur or phosphorus atom, the reaction may be carried out by or according to conventional or known methods. Examples of the acylating agents employed in the acylation include, for example, acyl halides and (mixed) acid anhydrides containing a group represented by $R^9$. Examples of the reacting agents employed in the alkoxycarbonylation, aryloxycarbonylation, aralkyloxycarbonylation, heterocycloxycarbonylation, and heterocycle-substituted alkoxycarbonylation include, for example, oxycarbonyl halides and carbonate esters containing a group represented by $R^{10}$. Examples of the reacting agents employed in the sulfenylation, sulfinylation, and sulfonylation include, for example, sulfenyl halides, sulfinyl halides, and sulfonyl halides, and sulfonic acid anhydrides containing a group represented by $R^{13}$. Examples of the reacting agents employed in the phosphorylation include, for example, phosphoryl halides containing groups represented by $R^{14}$ and $R^{15}$.

Preferred examples of the halogens in the above-mentioned reacting halides are bromine and chlorine. The reagent is preferably used in at least a molar equivalent per starting compound, more preferably in an amount of about 1 to 5 molar equivalents. When the acid anhydride is used as the acylating agent in the acylation, it can be employed in a large excess amount. The solvent employed in the reaction is not limited to but includes any as long as it dissolves the compound [I$^g$] and reagent. Preferred examples of the solvents include, for example, dichloromethane, chloroform, dichloroethane, tetrahydrofuran, dioxane, N,N-dimethylformamide, N,N-dimethylacetamide, dimethyl sulfoxide, hexamethylenephosphorotriamide, pyridine, acetonitrile, and the like.

In the reaction, the reaction temperature is usually in the range of $-50°$ to $150°$ C., and the reaction time is usually in the range of about 0.1 to 48 hours. For the purpose of accelerating the reaction or reducing the formation of by-product, the reaction may be performed in the presence of a base. Examples of the bases include, for example, amines such as triethylamine, dimethylaminopyridine, pyridine, N,N-dimethylaniline and N,N-diethylaniline; sodium hydride; potassium hydride; sodium amide; n-butyl lithium; lithium diisopropylethylamide; and the like.

(F) The compound [IX] or salt thereof is nitrated to form the nitroguanidine derivative [I].

The nitrating reagents include 60 to 100% nitric acid; alkali metal nitrates such as sodium nitrate and potassium nitrate; alkyl nitrate esters such as ethyl nitrate and amyl nitrate; nitronium tetrafluoroborate ($NO_2BF_4$); nitronium trifluoromethanesulfonate ($NO_2CF_3SO_3$); and the like. A preferred example of the nitrating reagent frequently used is 60 to 100% nitric acid. The nitrating reagent can be used in an amount of about 1.0 to 20 equivalents per compound [IX] or salt thereof, preferably about 2.0 to 10 equivalents in the case of nitric acid.

The reaction may be performed in the absence of solvent, but it is usually carried out in sulfuric acid, acetic acid, acetic anhydride, trifluoroacetic anhydride, trifluoromethanesulfonic acid, or the like as the solvent. As the case may be, the solvents and their mixture may be employed. The reaction temperature is usually in the range of $-50°$ to $100°$ C., preferably $-20°$ to $60°$ C. The reaction time is usually in the range of 10 minutes to 10 hours, preferably 30 minutes to 2 hours.

(G) The compound [I$^f$] or salt thereof is reacted with the compound [X] or [XI] to form the nitroguanidine derivative [I$^h$]. Preferred examples of the compounds [I$^f$] are those wherein at least one of $R^{2d}$ and $R^{3d}$ is the reactive ester such as $—COOR^{16}$ wherein $OR^{16}$ is capable of easily leaving. Examples of $R^{16}$ are 1-halogeno-$C_{1-4}$ alkyl such as 1-chloroethyl and polyhalogenophenyl such as 2,4,5-trichlorophenyl and 2,3,4,5,6-pentachlorophenyl.

The reaction is performed preferably in an organic solvent (optionally in the coexistence of water). Examples of the solvent include dichloromethane, chloroform, 1,2-dichloroethane, tetrahydrofuran, 1,4-dioxane, acetonitrile and the like. The compound [X] or [XI] can be used preferably in an amount of 1 to 20 molar equivalents. The reaction temperature and time can vary depending on the compound [X] or [XI] used; however, the reaction temperature is preferably in the range of $0°$ to $100°$ C. and the reaction time is preferably in the range of I minute to 168 hours. The resulting compound [I] or salt thereof can be isolated and purified by means known per se, e.g. concentration, vacuum concentration, distillation, fractional distillation, extraction with solvent, change of basicity, redistribution, chromatography, crystallization, recrystallization.

A substituted nitroguanidine compound of the formula [I$^o$]:

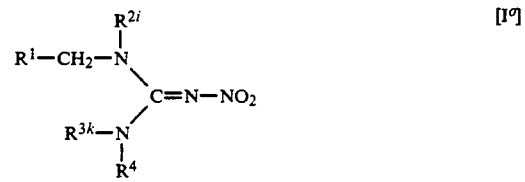

wherein $R^1$ has the same meaning as defined above; $R^{21}$ is hydrogen or a substituted or unsubstituted hydrocarbon group; $R^{3k}$ is a group attached through a carbonyl group except for formyl and acetyl, a group attached through a sulfur atom, a group attached through a phosphorus atom or cyano; and $R^4$ has the same meaning as defined above; or a salt thereof, is prepared by reacting a compound of the formula [XII]:

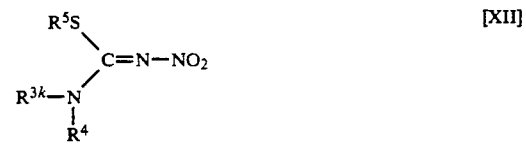

wherein $R^{3k}$, $R^4$ and $R^5$ have the same meanings as defined above, or a salt thereof, with a compound of the formula [XIII]:

wherein $R^1$ and $R^{2i}$ have the same meanings as defined above, or a salt thereof.

The starting compound [XII] or salt thereof is reacted with the compound [XIII] or salt thereof to form the nitroguanidine derivative [I$^o$]. Preferred examples of $R^5$ and the reaction conditions are the same as those stated in Process (A).

The compounds [II] and [XII] or salts thereof which are employed as the starting materials for preparing the compounds of the present invention can be prepared, for example, from the compounds described in European Patent Application Laid Open No. 0,376, 279/1990 by Processes (D) and (E) of the present invention or methods similar or analogous thereto.

The compounds [$I^c$], [$I^g$], and [$I^i$] or salts thereof are included in the compounds [I] of the present invention and can be prepared by the processes as above-mentioned.

The amine [III], [X], [XI] or salt thereof can be prepared, for example by the method described in "Survey of Organic Synthesis," Wiley-Interscience (1970), Chapter 8, and "SHIN JIKENKAGAKU KOZA (New Experimental Chemistry Handbook)," Maruzen Publishing Co., Ltd., Japan, Vol. 14-III, pp. 1332-1399 or methods similar thereto.

The amino compound [XII] or salt thereof can be prepared, for example by the method described in "Organic Functional Group Preparations," Academic Press, Vol.1, Chapter 13 (1968), and Vol.3, Chapter 10 (1972), or by the method described in Japanese Patent Laid Open Nos. 171/1990 and 333721/1989, or methods similar thereto.

The compound [V] or salt thereof can be prepared, for example by the method described in "Organic Functional Group Preparations," Academic Press, Vol.1, Chapter 6 (1968), and Japanese Patent Laid Open Nos. 171/1990, or methods similar thereto.

The compound [VII, [VIII, [VIII] or salts thereof can be prepared, for example by the method described in "SHIN JIKENKAGAKU KOZA (New Experimental Chemistry Handbook)," Maruzen Publishing Co., Ltd., Japan, Vol. 14-I, pp. 307-450, and Vol. 14-II, pp. 1104-1133 or methods similar thereto.

The compound [IV], [IX] or salts thereof can be prepared, for example by the method described in "Rodd's Chemistry of Carbon Compounds, Vol. 1, Part c, pp. 341-353, and "Chemical Reviews,"51, 301 (1952), or methods similar thereto.

A valuable group of novel substituted nitroguanidine derivatives are the compounds having the following formula [A]:

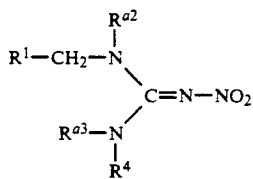

wherein $R^1$ is a substituted or unsubstituted heterocyclic group; $R^{a2}$ is hydrogen, a substituted or unsubstituted hydrocarbon group (except for one substituted with an oxo group at the binding site), or —CO—$R^{9a}$, wherein $R^{9a}$ is hydrogen, a substituted or unsubstituted hydrocarbon group or a substituted or unsubstituted heterocyclic group; $R^{a3}$ is a group attached through a sulfur atom, a group attached through a phosphorus atom, cyano or —CO—NR$^{7a}$R$^{8a}$, wherein R$^{7a}$, and R$^{8a}$, which are the same or different, are each independently hydrogen, a substituted or unsubstituted hydrocarbon group or a substituted or unsubstituted heterocyclic group, or R$^{7a}$ and R$^{8a}$, taken together with the nitrogen atom to which they are attached are a cyclic amino group; and $R^4$ is hydrogen or a lower alkyl group; and salts thereof, which have unexpectedly potent pesticidal activity and very low toxicity.

Another valuable group of novel substituted nitroguanidine derivatives are the compounds having the following formula [B]:

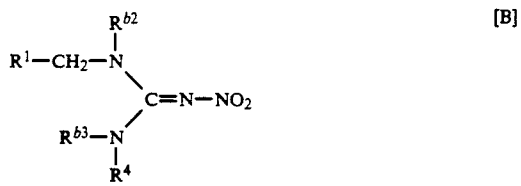

wherein $R^1$ is a substituted or unsubstituted heterocyclic group; $R^{b2}$ is —CO—$R^{9b}$ wherein $R^{9b}$ is hydrogen or a substituted or unsubstituted hydrocarbon group or a substituted or unsubstituted heterocyclic group; $R^{b3}$ is hydrogen, a substituted or unsubstituted hydrocarbon group (except for one substituted with an oxo group at the binding site), —CO—$R^{9c}$ wherein $R^{9c}$ is a substituted or unsubstituted hydrocarbon group or a substituted or unsubstituted heterocyclic group or —CO—OR$^{10a}$ wherein R$^{10a}$ is a substituted or unsubstituted hydrocarbon group or a substituted or unsubstituted heterocyclic group; and $R^4$ is hydrogen or a lower alkyl group; and salts thereof, which have unexpectedly potent pesticidal activity and very low toxicity.

More valuable substituted nitroguanidine derivatives are the compounds having the following formula [C]:

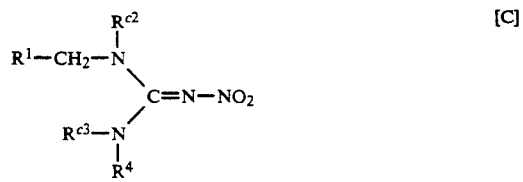

wherein $R^1$ is a substituted or unsubstituted heterocyclic group; $R^{c2}$ is —CO—$R^{9b}$ wherein $R^{9b}$ is hydrogen or a substituted or unsubstituted hydrocarbon group or a substituted or unsubstituted heterocyclic group; $R^{c3}$ is hydrogen or a substituted or unsubstituted hydrocarbon group (except for one substituted with an oxo group at the binding site); and $R^4$ is hydrogen or a lower alkyl group; and salts thereof, which have unexpectedly potent pesticidal activity and very low toxicity.

Still more valuable substituted nitroguanidine derivatives are the compounds having the following formula [D]:

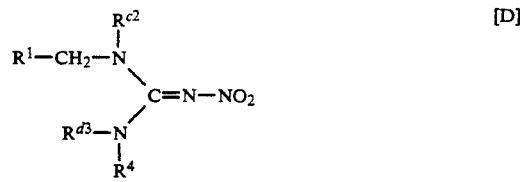

wherein $R^1$ is a substituted or unsubstituted heterocyclic group; $R^{c2}$ is —CO—$R^{9b}$ wherein $R^{9b}$ is hydrogen or a substituted or unsubstituted hydrocarbon group or a substituted or unsubstituted heterocyclic group; $R^{d3}$ is hydrogen; and $R^4$ is hydrogen or a lower alkyl group; and salts thereof, which have unexpectedly potent pesticidal activity and very low toxicity.

Among the compounds represented by the above formula (D), a preferred embodiment of the disclosure is a compound of the formula:

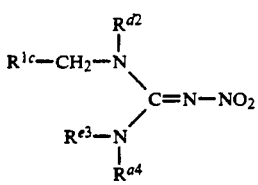

[E]

wherein $R^{1c}$ is pyridyl, halogenopyridyl, thiazolyl, or halogenothiazolyl; $R^{d2}$ is $C_{1-4}$ carboxylic acyl such as formyl, acetyl and propionyl; $R^{e3}$ is hydrogen, or $C_{1-4}$ alkyl such as methyl, ethyl and propyl; and $R^{a4}$ is hydrogen or $C_{1-4}$ alkyl such as methyl, ethyl and propyl; or a salt thereof. Specific examples of the substituent groups for $R^{1c}$ are, for example, halogenopyridyl such as 6-chloro-3-pyridyl, 6-bromo-3-pyridyl and 5-bromo-3-pyridyl, or halogenothiazolyl such as 2-chloro-5-thiazolyl and 2-bromo-5-thiazolyl.

Among the compounds represented by the above formula (D), a more preferred embodiment of the disclosure is a compound of the formula:

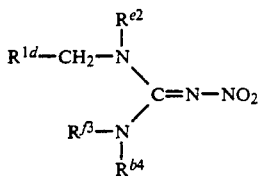

[F]

wherein $R^{1d}$ is pyridyl, halogenopyridyl, thiazolyl, or halogenothiazolyl; $R^{e2}$ is $C_{1-4}$ carboxylic acyl such as formyl, acetyl and propionyl; $R^{f3}$ is hydrogen; and $R^{b4}$ is $C_{1-4}$ alkyl such as methyl, ethyl and propyl; or a salt thereof. Specific examples of the substituent groups for $R^{1d}$ are, for example, halogenopyridyl such as 6-chloro-3-pyridyl, 6-bromo-3-pyridyl and 5-bromo-3-pyridyl, or halogenothiazolyl such as 2-chloro-5-thiazolyl and 2-bromo-5-thiazolyl.

The hydrocarbon group in the "substituted or unsubstituted hydrocarbon group" for $R^{a2}$, $R^{9a}$, $R^{9b}$, $R^{9c}$, $R^{7a}$, $R^{8a}$, $R^{b3}$, $R^{c3}$ and $R^{10a}$, includes those groups mentioned in the substituent group for $R^1$.

The substituent group on the "substituted or unsubstituted hydrocarbon group" for $R^{a2}$, $R^{9a}$, $R^{9b}$, $R^{9c}$, $R^{7a}$, $R^{8a}$, $R^{b3}$, $R^{c3}$, $R^{c3}$ and $R^{10a}$ includes those mentioned in the substituent group on the heterocyclic group for $R^1$.

The heterocyclic group in the "substituted or unsubstituted heterocyclic group" for $R^{9a}$, $R^{9b}$, $R^{9c}$, $R^{7a}$, $R^{8a}$, and $R^{10a}$ includes those groups mentioned herein for $R^1$.

The substituent group on the "substituted or unsubstituted heterocyclic group" for $R^{9a}$, $R^{9b}$, $R^{9c}$, $R^{7a}$, $R^{8a}$, and $R^{10a}$ includes those mentioned in the substituent group on the heterocyclic group for $R^1$.

The group attached through a sulfur atom for $R^{a3}$ includes those groups mentioned herein for $R^2$ and $R^3$.

The group attached through a phosphorus atom for $R^{a3}$ includes those groups mentioned herein for $R^2$ and $R^3$.

Examples of the salts of the guanidine derivatives [A], [B], [C], [D], [E], and [F] include salts with inorganic acids such as hydrochloric acid, hydrobromic acid, hydriodic acid, phosphoric acid, sulfuric acid, and perchloric acid, as well as organic acids such as formic acid, acetic acid, tartaric acid, malic acid, citric acid, oxalic acid, succinic acid, benzoic acid, picric acid, and p-toluenesulfonic acid.

The substituted nitroguanidine derivatives [A], [B], [C], [D], [E], and [F] or salts thereof can be employed as insecticide in any application form suitable for conventional agricultural chemicals in the same manner mentioned herein for the substituted nitroguanidine derivatives [I].

These substituted nitroguanidine derivatives and their salts can be prepared by Processes (A) to (G) described herein or according to methods similar or analogous thereto.

In the case where the substituted nitroguanidine derivative is obtained in its free form, it can be converted into the corresponding salt as mentioned above by conventional methods. When the substituted nitroguanidine derivative is obtained in its salt form, it can be converted into the corresponding free form by conventional methods. Also, any substituted nitroguanidine derivative may be in any of free or salt form when it is used as a raw material for preparing another substituted nitroguanidine derivatives. Other raw materials which can form salts can be employed as any of free or salt form. Accordingly, raw materials to be employed and products in the above-mentioned Processes include their respective salts (e.g. salts with the acids as mentioned above ).

The substituted nitroguanidine derivatives or salts thereof form cis and trans stereoisomers with respect to the position of the substituent $NO_2$ and can theoretically form tautomers when at least one of $R^{2aa}$, $R^{3aa}$ and $R^{4aaa}$ is hydrogen. The compounds [I] or their salts of the present invention include such isomers, i.e. the mixture of isomers and the individual stereoisomers.

Scheme 1:

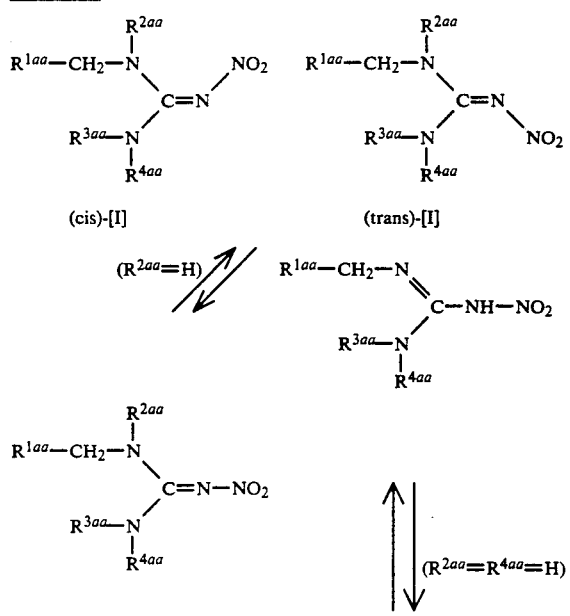

-continued
Scheme 1:

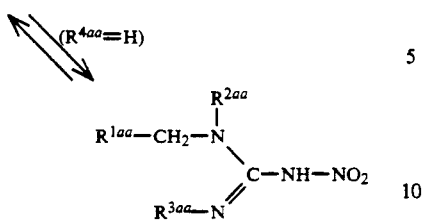

wherein $R^{1aa}$, $R^{3aa}$ and $R^{4aa}$ have the same meanings as defined herein for $R^1$, $R^3$ and $R^4$, respectively and $R^{2aa}$ is hydrogen, a substituted or unsubstituted hydrocarbon group (except for one substituted with an oxo group at the binding site), a group attached through a sulfur atom, a group attached through a phosphorus atom, cyano, —CO—$R^{9aa}$ wherein $R^{9aa}$ is a substituted or unsubstituted hydrocarbon group or a substituted or unsubstituted heterocyclic group, —CO—OR$^{6aa}$ wherein $R^{6aa}$ is a substituted or unsubstituted hydrocarbon group or a substituted or unsubstituted heterocyclic group, or —CO—NR$^{7aa}$ R$^{8aa}$ wherein $R^{7aa}$ and $R^{8aa}$, which are the same or different, are each independently hydrogen, a substituted or unsubstituted hydrocarbon group or a substituted or unsubstituted heterocyclic group, or $R^{7aa}$ and $R^{8aa}$, taken together with the nitrogen atom to which they are attached are a cyclic amino group.

Activity

The substituted nitroguanidine derivatives (I) and the salts thereof have potent pesticidal activity as supported by the following test examples.

TEST EXAMPLE 1

Effect Against Nilaparvata Lugens

Five milligrams each of test compounds (designated by each compound number assigned to the compound prepared in an Example as described hereinafter) were respectively dissolved in 0.5 ml of acetone containing Tween 20 TM and diluted with a 3,000-fold aqueous solution of Dyne TM (spreading agent manufactured by Takeda Chemical Industries, Ltd.) to a predetermined concentration (100 ppm). This solution was applied to the leaves and stems of rice seedlings at the 2-leaf stage raised in a nursery box at a rate of 10 ml/pot by a spray gun. The treated rice seedlings were placed into test tubes of which the bottom space had been filled with water. After the release of 10 third-enstar larvae of Nilaparvata lugens to the test tube, the tube was sealed with an aluminum cap followed by incubation at 25° C. in a thermostatic room. The number of dead insects was counted 7 days after release. The mortality rate was calculated by means of the following equation and summarized in Table 1.

$$\text{Mortality (\%)} = \frac{\text{Number of dead insects}}{\text{Number of insects released}} \times 100$$

TABLE 1

| Compound No. | Mortality (%) |
| --- | --- |
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 11 | 100 |
| 12 | 100 |
| 13 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |

Table 1 demonstrates the excellent pesticidal activity of the substituted nitroguanidine derivatives (I) and the salts thereof against Nilaparvata lugens.

TEST EXAMPLE 2

Effect Against Spodoptera Litura

One milligrams each of test compounds (designated by each compound number assigned to the compound prepared in an Example as described hereinafter) were respectively dissolved in 0.5 ml of acetone containing Tween 20 TM and diluted with a 3,000-fold aqueous solution of Dyne TM to a predetermined concentration (100 ppm). This solution was applied to soybean seedlings at the simple leaf unfolding stage at a rate of 20 ml/pot by a spray gun. After the chemical solution had dried, two simple leaves per seedling were shorn off and placed into an ice cream cup to which 10 third-instar larvae of Spodoptera litura were released. After the release, the cup was placed in an incubator at 25° C. The number of dead insects was counted 2 days after release. The mortality rate was calculated by means of the equation given in Test Example 1 and summarized in Table 2.

TABLE 2

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 9 | 100 |
| 12 | 100 |
| 13 | 100 |
| 15 | 100 |
| 18 | 100 |
| 19 | 100 |
| 20 | 100 |
| 21 | 100 |
| 22 | 100 |
| 23 | 100 |
| 24 | 100 |
| 26 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |

Table 2 demonstrates the excellent pesticidal activity of the substituted nitroguanidine derivatives (I) and the salts thereof against *Spodoptera litura*.

TEST EXAMPLE 3

Effect Against Aphis Gossypii

Five milligrams each of test compounds (designated by each compound number assigned to the compound prepared in an Example as described hereinafter) were respectively dissolved in 0.5 ml of acetone containing Tween 20 TM and diluted with a 3,000-fold aqueous solution of Dyne TM to a predetermined concentration (100 ppm). This solution was applied at a rate of 10 ml/pot by a spray gun to the leaves and stems of *Cucumis sativus* at the first leaf unfolding stage to which 10 female adults of *Aphis gossypii* had been released one day before spraying. The tested plant was placed in a glass incubator at 27° C. The number of survived insects was counted 2 days after the treatment. The mortality rate was calculated by means of the following equation and summarized in Table 3.

$$\text{Mortality (\%)} = \frac{\text{Number of insects released} - \text{Number of insects survived}}{\text{Number of insects released}} \times 100$$

TABLE 3

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 11 | 100 |
| 12 | 100 |
| 13 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 53 | 100 |
| 54 | 100 |
| 55 | 100 |
| 56 | 100 |
| 57 | 100 |

Table 3 demonstrates the excellent pesticidal activity of the substituted nitroguanidine derivatives (I) and the salts thereof against *Aphis gossypii*.

The following examples and reference examples are intended to illustrate the invention in further detail and should by no means be construed as limiting the scope of the invention.

The procedure of elution in column chromatography as described in Examples and Reference Examples was carried out under monitoring by thin layer chromatography (TLC). In TLC monitoring, Merck's Kieselgel 60F$_{254}$ (70-230 mesh, Merck Co.) was used as the TLC plate; the developing solvent was the same as that used for eluting in the column chromatography; and a UV detector was used for detection. The silica gel for column chromatography was Kieselgel 60 (70-230 mesh, a product manufactured by Merck Co.). NMR spectra were recorded by proton NMR, and measured using tetramethylsilane as an internal reference standard with Varian EM390 (90MHz) or Hitachi R-600 (60 MHz)

spectrometer. All δ values are expressed in ppm. The numerals given in parentheses for a mixed solvent as the developing solvent represent a volume ratio of the ingredients thereof.

The abbreviations used in the following Examples, Reference Examples and Tables 4-5 have the following meanings.

Me: methyl, Et: ethyl, Ph: phenyl, s: singlet, br: broad, d: doublet, t: triplet, q: quartet, m: multiplet, dd: doublet of doublets, J: coupling constant, Hz: hertz, CDCl$_3$: deuteriochloroform, DMSO-d$_6$: deuteriodimethylsulfoxide, %: wt %, mp: melting point. The term "room temperature" means about 15°-25° C.

REFERENCE EXAMPLE 1

To a stirred mixture of S-methyl-N-nitroisothiourea (0.30 g) and pyridine (5 ml) was added 1.05 g of isobutyric anhydride dropwise at room temperature (slightly exothermically). After stirring for 1 hour at room temperature and standing overnight, the reaction mixture was poured into 80 ml of 2N hydrochloric acid. The resulting mixture was extracted with 100 ml of Et$_2$O, dried over MGSO$_4$ and concentrated in vacuo to afford 0.38 g of N-isobutyroyl-S-methyl-N'-nitroisothiourea as pale yellow oil. NMR(CDCl$_3$)δ: 1.29(d, J=7.2Hz, 6H), 2.30-2.94(m, 1H), 2.46(s, 3H)

REFERENCE EXAMPLE 2

To a stirred mixture of S-methyl-N-nitroisothiourea (1.0 g) and pyridine (10 ml) was added 1.4 g of methyl chlorocarbonate dropwise below −9° C. under cooling. After stirring for 1 hour at −13° C., for 30 minutes at 0° C. and then for 3 hour at room temperature, 1.4 g of methyl chlorocarbonate was added dropwise to the reaction mixture below 14° C. under cooling. After stirring at room temperature for 1.5 hours, 1.4 g of methyl chlorocarbonate was added dropwise to the reaction mixture below 11° C. under cooling. After stirring at room temperature for I hour, the reaction mixture was poured into a mixture of ice (50 g) and 2N hydrochloric acid (50 ml) and the resulting precipitated crystals were seperated by filtration and dried to afford 0.50 g of white crystals. The filtrate was acidified with hydrochloric acid, extracted with 100 ml of AcOEt, dried and concentrated to afford 0.72 g of yellow cryistals. The combined crystals were recrystallized from toluenehexane to yield 1.0 g of N-methoxycarbonyl-S-methyl-N'-nitroisothiourea as a white crystal. Recrystallization of the product from toluene gave m.p. 90-°93.5° C. NMR(CDCl$_3$)δ: 2.43(s, 3H), 3.86(s, 3H), 11.09(br, 1H)

REFERENCE EXAMPLE 3

A mixture of N-(2-chloro-5-thiazolylmethyl)-S-methyl-N'-nitroisothiourea (1.00 g), pyridine (2.37 9), CH$_2$Cl$_2$ (12 ml) and CH$_3$CN (12 ml) was cooled to 4° C. To the cooled mixture was added 1.14 g of n-valeroyl chloride dropwise over 1 minute under stirring. After 5 minutes, the cooling bath was removed and then the mixture was stirred at room temperature for 1 hour. To the mixture was added 0.23 g of n-valeroyl chloride three times intervally 20, 145, and 165 minutes later and 0.30 g, 0.30 g and 1.2 g of pyridine 115, 200, and 220 minutes later, respectively and the mixture was continued to be stirred at room temperature. After 230 minutes, a mixed solution of conc. hydrochloric acid (3 ml) and water (22 ml) was added to the mixture followed by partition. The aqueous layer was extracted with CH$_2$Cl$_2$ (25 ml×2). The combined organic layers were washed with brine, dried over MGSO$_4$ and evaporatedin vacuo. The resulting residue was applied to column chromatography on silica gel. The column was eluted with CHCl$_3$-EtOH (20:1) to afford 1.50 g of N-(2-chloro-5-thiazolylmethyl)-S-methyl-N'-nitro-N-n-valeroylisothiourea as a pale yellow oil. NMR(CDCl$_3$)δ: 0.7-2.0(m, 7H), 2.3-2.7(m, 2H), 2.5(s, 3H), 4.8(s, 3H), 7.5(s, 1H)

REFERENCE EXAMPLE 4

A mixture of N-(2-chloro-5-thiazolylmethyl)-S-methyl-N'-nitroisothiourea (0.93 g), pyridine (3 ml) and CH$_3$CN (3 ml) was cooled with iced water. To the cooled mixture was added 1.05 g of benzoyl chloride dropwise below 6° C. over 1 minute under stirring. After the addition, the cooling bath was removed and then the mixture was stirred at room temperature for 85 minutes. To the mixture was added a mixed solution of conc. hydrochloric acid (7 ml) and water (25 ml) and the resulting mixture was extracted with CHCl$_3$ (70 ml). The aqueous layer was extracted with CHCl$_3$ (20 ml×3) and the combined organic layers were washed with brine, dried over MgSO$_4$ and evaporated in vacuo. The resulting residue was applied to column chromatography on silica gel. The column was eluted with first CHCl$_3$ and next CHCl$_3$-ETOH (30:1 and next 20:1) to afford crude products which were purified by column chromatography on silica gel [hexane-AcOEt (2:1)]to yield 0.93 g of N-benzoyl-N-(2-chloro-5-thiazolylmethyl)-S-methyl-N'-nitroisothiourea as a pale yellow oil.

NMR(CDCl$_3$)δ: 2.28(s, 3H), 5.12(s, 2H), 7.20-7.85(m, 6H)

REFERENCE EXAMPLE 5

The procedure of Reference Example 4 was repeated replacing the benzoyl chloride with phenyl chloroformate to obtain N-(2-chloro-5-thiazolylmethyl)-S-methyl-N'-nitro-N-phenoxycarbonylisothiourea as a pale yellow oil.

NMR(CDCl$_3$)δ:2.48(s, 3H), 4.95(s, 2H), 6.95-7.45(m, 5H), 7.57(s, 1H)

REFERENCE EXAMPLE 6

The procedure of Reference Example 4 was repeated replacing the benzoyl chloride with 1-chloroethyl chloroformate to obtain N-(1-chloroethoxycarbonyl)-N-(2-chloro-5-thiazolylmethyl)-S-methyl-N'-nitroisothiourea as a pale yellow oil.

NMR(CDCl$_3$)δ5: 1.84(d, J=6 Hz, 3H), 2.98(s, 3H), 4.90(s, 2H), 6.50(q, J=6 Hz, 1H), 7.55(s, 1H)

REFERENCE EXAMPLE 7

A mixture of S-methyl-N-nitroisothiourea (5.0 g), CH$_3$CN (50 ml) and Et$_3$N (11.2 g) was cooled with iced water. To the cooled mixture was added 10.6 g of n-propanesulfonyl chloride dropwise below 15° C. under stirring. After stirring at the same temperature for 1 hour, the mixture was poured into a mixed solution of conc. hydrochloric acid (20 ml) and water (180 ml) and the resulting mixture was extracted with AcOEt. The organic layer was dried over MgSO$_4$ and concentrated in vacuo to afford 9.9 g of crude crystals. Recrystallization of the product from CCl$_4$ (5 ml) gave 5.4 g of S-methyl-N-nitro-N'-(n-propanesulfonyl)isothiourea as a pale yellow crystal, m.p. 91°-93° C.

NMR(CDCl$_3$)δ:1.12(t, J=7.2 Hz, 3H), 1.75-2.13(m, 2H), 2.47(s, 3H), 3.19-3.46(m, 2H), 9.62(br, 1H)

REFERENCE EXAMPLE 8

The procedure of Reference Example 4 was repeated replacing the N-(2-chloro-5-thiazolylmethyl)-S-methyl-N'-nitroisothiourea and the benzoyl chloride with S,N-dimethyl-N'-nitroisothiourea and 1-chloroethyl chloroformate to obtain N-(1-chloroethoxycarbonyl)-S, N-dimethyl-N'-nitroisothiourea as an orange oil.

NMR(CDCl$_3$)δ:1.82(d, J=6 Hz, 3H), 2.50(s, 3H), 3.27(s, 3H), 6.48(q, J=6 Hz, 1 H)

REFERENCE EXAMPLE 9

The procedure of Reference Example 4 was repeated replacing the N-(2-chloro-5-thiazolylmethyl)-S-methyl-N'-nitroisothiourea and the benzoyl chloride with S,N-dimethyl-N'-nitroisothiourea and phenyl chloroformate to obtain S,N-dimethyl-N-phenoxycarbonyl-N'-nitroisothiourea as a yellow oil.

NMR(CDCl$_3$)δ: 2.53(s, 3H), 3.33(s, 3H), 7.0–7.6(m, 5H)

REFERENCE EXAMPLE 10

The procedure of Reference Example 7 was repeated replacing the n-propanesulfonyl chloride and the S-methyl-N-nitroisothiourea with methanesulfonyl chloride and S,N-dimethyl-N'-nitroisothiourea to obtain S,N-dimethyl-N-methanesulfonyl-N'-nitroisothiourea as a oil.

NMR(CDCl$_{33}$)13: 2.57(s, 3H), 3.23(s, 3H), 3.33(s, 3H)

REFERENCE EXAMPLE 11

The procedure of Reference Example 4 was repeated replacing the N-(2-chloro-5-thiazolylmethyl)-S-methyl-N'-nitroisothiourea and the benzoyl chloride with S,N-dimethyl-N'-nitroisothiourea and methyl chloroformate to obtain S,N-dimethyl-N-methoxycarbonyl-N'-nitroisothiourea as a pale yellow crtstal, m.p. 46°–47° C.

NMR(CDCl$_3$)δ: 2.49(s, 3H), 3.26(s, 3H), 3.79(s, 3H)

REFERENCE EXAMPLE 12

The procedure of Reference Example 4 was repeated replacing the benzoyl chloride with methyl chloroformate to obtain N-(2-chloro-5-thiazolylmethyl)-N-methoxycarbonyl-S-methyl-N'-nitroisothiourea as an oil.

NMR(CDCl$_3$)δ: 2.47(s, 3H), 3.82(s, 3H), 4.90(s, 2 H), 7.55(s, 1H)

REFERENCE EXAMPLE 13

To a mixture of S,N-dimethyl-N'-nitroisothiourea (0.5 g), CH$_3$CN (20 ml) and potassium carbonate (0.93 g) was added a solution of phenylacetyl chloride (1.04 g) in CH$_3$CN (2 ml) dropwise at room temperature over 10 minutes under stirring. After stirring for 3 hours, insolubles were filtered off and the filtrate was concentrated in vacuo. The resulting residue was applied to column chromatography on silica gel. The column was eluted with hexaneacetone (2:1) to afford 0.54 g of S,N-dimethyl-N'-nitro-N-phenylacetylisothiourea as an oil.

NMR(CDCl$_3$)δ: 2.27(s, 3H), 3.15(s, 3H), 3.88(s, 2H), 7.28(s, 5H)

REFERENCE EXAMPLE 14

The procedure of Reference Example 13 was repeated replacing the S,N-dimethyl-N'-nitroisothiourea with N-(2-chloro-5-thiazolylmethyl)-S-methyl-N'-nitroisothiourea to obtain N-(2-chloro-5-thiazolylmethyl)-S-methyl-N'-nitro-N-phenylacetylisothiourea as an oil.

NMR(CDCl$_3$)δ: 2.30(s, 3H), 3.87(s, 2H), 4.78(s, 2H), 7.29(s, 5H), 7.48(s, 1H)

REFERENCE EXAMPLE 15

The procedure of Reference Example 13 was repeated replacing the phenylacetyl chloride with 2-thiophenecarbonyl chloride to obtain S,N-dimethyl-N'-nitro-N-(2-thiophenecarbonyl)isothiourea as an oil.

NMR(CDCl$_3$)δ: 2.45(s, 3H), 3.38(s, 3H), 7.0–7.2(m, 1H), 7.5–7.8(m, 2H)

REFERENCE EXAMPLE 16

The procedure of Reference Example 13 was repeated replacing the S,N-dimethyl-N'-nitroisothiourea and the phenylacetyl chloride with N-(2-chloro-5-thiazolylmethyl)-S-methyl-N'-nitroisothiourea and 2-thiophenecarbonyl chloride to obtain N-(2-chloro-5-thiazolylmethyl)-S-methyl-N'-nitro-N-(2-thiophenecarbonyl)isothiourea as an oil.

NMR(CDCl$_3$) δ: 2.37(s, 3H), 5.04(s, 2H), 7.0–7.2(m, 1H), 7.58(s, 1H), 7.5–7.8(m, 2H)

REFERENCE EXAMPLE 17

The procedure of Reference Example 13 was repeated replacing the phenylacetyl chloride with benzyl chloroformate to obtain N-benzyloxycarbonyl-S,N-dimethyl-N'-nitroisothiourea as an oil.

NMR(CDCl$_3$)δ: 2.42(s, 3H), 3.25(s, 3H), 5.18(s, 2H), 7.35(s, 5H)

REFERENCE EXAMPLE 18

The procedure of Reference Example 13 was repeated replacing the S,N-dimethyl-N'-nitroisothiourea and the phenylacetyl chloride with N-(2-chloro-5-thiazolylmethyl)-S-methyl-N'-nitroisothiourea and benzyl chloroformate to obtain N-benzyloxycarbonyl-N-(2-chloro-5-thiazolylmethyl)-S-methyl-N'-nitroisothiourea as an oil.

NMR(CDCl$_3$)δ: 2.38(s, 3H), 4.90(s, 2H), 5.22(s, 2H), 7.38(s, 5H), 7.50(s, 1H)

REFERENCE EXAMPLE 19

To a cooled, stirred mixture of S,N-dimethyl-N'-nitroisothiourea (1.0 g), triethylamine (0.68 g) and DMF (10 ml) was added 1.2 g of trichloromethanesulfenyl chloride dropwise at 3°–7° C. After stirring at the same temperature for 1 hour, the mixture was poured into 50 ml of 2N hydrochloric acid and the resulting mixture was extracted with toluene (50 ml). The toluene layer was washed with water (50 ml), dried over MgSO$_4$ and concentrated in vacuo. The resulting residue was applied to column chromatography on silica gel. The column was eluted with hexane-AcOEt (8:1). The fractions containing the desired product were concentrated to afford 1.1 g of S,N-dimethyl-N'-nitro-N-trichloromethanesulfenylisothiourea as a pale yellow crystal, m.p. 75°–78° C.

NMR(CDCl$_3$)δ: 2.48(s, 3H), 3.69(s, 3H)

The following compounds listed in Table 4 below were prepared by employing S,N-dimethyl-N'-nitroisothiourea (M) or N-(2-chloro-5-thiazolylmethyl)-S-methyl-N'-nitroisothiourea (T) and the acylating reagents, bases and reaction solvents listed in Table 4 according to the procedures of Reference Examples 1–19 or the analogues thereof.

TABLE 4

$$\begin{array}{c} \text{MeS} \\ \diagdown \\ \text{C}=\text{N}-\text{NO}_2 \\ \text{R}^A-\text{CO}-\text{N} \\ | \\ \text{CH}_2\text{R}^B \end{array}$$

| Ref. Ex No. | $R^A$ | $R^B$ | mp (°C.) | NMR(solvent)δ: | * | Acylating Agent | Base | Reaction Solvent |
|---|---|---|---|---|---|---|---|---|
| 20 | $^i$Pr | H | (oil) | (CDCl₃): 1.15(d, 6H), 2.50(s, 3H), 3.15(s, 3H) | M | ($^i$PrCO)₂O | pyridine | CH₃CN |
| 21 | $^t$Bu-C₆H₄- | H | 65-68 | (CDCl₃): 1.31(s, 9H), 2.38(s, 3H), 3.38(s, 3H), 7.30~7.75(m, 4H) | M | $^t$Bu-C₆H₄-COCl | K₂CO₃ | CH₃CN |
| 22 | Et | Cl-C(=N)-S-CH=C(CH₃)- | (oil) | (CDCl₃): 1.17(t, J=7.2Hz, 3H), 2.50(s, 3H), 2.54(q, J=7.2Hz, 2H), 4.77(s, 2H), 7.50(s, 1H) | T | (EtCO)₂O | pyridine | pyridine |
| 23 | $^n$Pr | Cl-C(=N)-S-CH=C(CH₃)- | (oil) | CDCl₃): 0.75~1.17(m, 3H), 1.18~2.07(m, 2H), 2.28~2.65(m, 2H), 2.51(s, 3H), 4.77(s, 2H), 7.50 | T | $^n$PrCOCl | pyridine | CH₂Cl₂ |
| 24 | $^i$Pr | Cl-C(=N)-S-CH=C(CH₃)- | (oil) | (CDCl₃): 1.17(d, J=6.6Hz, 6H), 2.30~2.98(m, 1H), 2.50(s, 3H), 4.77(s, 2H), 7.50(s, 1H) | T | ($^i$PrCO)₂O | pyridine | pyridine |
| 25 | $^i$Bu | Cl-C(=N)-S-CH=C(CH₃)- | (oil) | (CDCl₃): 0.95(d, J=6Hz, 6H), 1.27(m, 1H), 2.00~2.50(m, 2H), 2.51(s, 3H), 4.78(s, 2H), 7.50(s, 1H) | T | $^i$BuCOCl | K₂CO₃ | CH₃CN |
| 26 | Et | H | (oil) | (CDCl₃): 1.12(t, 3H), 2.47(q, 2H), 2.50(s, 3H), 3.15(s, 3H) | M | (EtCO)₂O | K₂CO₃ | CH₃CN |
| 27 | $^n$Pr | H | (oil) | (CDCl₃): 0.90(t, 3H), 1.65(m, 2H), 2.42(t, 2H), 2.50(s, 3H), 3.12 (s, 3H) | M | $^n$PrCOCl | K₂CO₃ | CH₃CN |
| 28 | $^n$Bu | H | (oil) | (CDCl₃): 0.6~1.9(m, 7H), 2.2~2.6 (m, 2H), 2.50(s, 3H), 3.15(s, 3H) | M | $^n$BuCOCl | K₂CO₃ | CH₃CN |
| 29 | $^i$Bu | H | (oil) | (CDCl₃): 0.95(d, 6H), 2.3(m, 3H), 2.50(s, 3H), 3.13(s, 3H) | H | $^i$BuCOCl | pyridine | CH₃CN |
| 30 | EtO | H | (oil) | (CDCl₃): 1.28(t, 3H), 2.48(s, 3H), 3.25(s, 3H), 4.20(q, 2H) | M | ClCOOEt | K₂CO₃ | CH₃CN |
| 31 | $^n$BuO | H | (oil) | (CDCl₃): 0.7~2.0(m, 7H), 2.46(s, 3H), 3.22(s, 3H), 4.15(t, 2H) | M | ClCOOBu$^n$ | K₂CO₃ | CH₃CN |
| 32 | $^i$BuO | H | (oil) | (CDCl₃): 0.94(d, 6H), 1.8~2.2(m, 1H), 2.48(s, 3H), 2.32(s, 3H), 3.95(d, 2H) | H | ClCOOBu$^i$ | K₂CO₃ | CH₃CN |
| 33 | $^t$BuO | H | (oil) | (CDCl₃): 1.45(s, 9H), 2.45(s, 3H), 3.20(s, 3H) | M | ($^t$BuOCO)₂O | K₂CO₃ | CH₃CN |
| 34 | EtO | Cl-C(=N)-S-CH=C(CH₃)- | (oil) | (CDCl₃): 1.32(t, J=7.2Hz, 3H), 2.47(s, 3H), 4.27(q, J=7.2Hz, 2H), 4.90(s, 2H), 7.54(s, 1H) | T | ClCOOEt | K₂CO₃ | CH₃CN |
| 35 | $^n$PrO | Cl-C(=N)-S-CH=C(CH₃)- | (oil) | (CDCl₃): 0.96(t, J=7.2Hz, 3H), 1.50~1.98(m, 2H), 2.46(s, 3H), 4.17(t, J=7.2Hz, 2H), 4.89(s, 2H), 7.53(s, 1H) | T | ClCOOPr$^n$ | K₂CO₃ | CH₃CN |
| 36 | $^i$PrO | Cl-C(=N)-S-CH=C(CH₃)- | (oil) | (CDCl₃): 1.31(d, J=7.2Hz, 6H), 2.46(s, 3H), 4.75~5.28(m, 1H), 4.89(s, 2H), 7.52(s, 1H) | T | ClCOOPr$^i$ | K₂CO₃ | CH₃CN |
| 37 | $^n$BuO | Cl-C(=N)-S-CH=C(CH₃)- | (oil) | (CDCl₃): 0.75~1.12(m, 3H), 1.13~1.85(m, 4H), 2.46(s, 3H), 3.95~4.37 (m, 2H), 4.89(s, 2H), 7.54(s, 1H) | T | ClCOOBu$^n$ | K₂CO₃ | CH₃CN |

TABLE 4-continued $$\begin{array}{c} \text{MeS} \\ \diagdown \\ \text{R}^A\text{—CO—N} \end{array} \text{C=N—NO}_2$$
$$\quad\quad\quad |$$
$$\quad\quad \text{CH}_2\text{R}^B$$

| Ref. Ex No. | $R^A$ | $R^B$ | mp (°C.) | NMR(solvent)δ: | * | Acylating Agent | Base | Reaction Solvent |
|---|---|---|---|---|---|---|---|---|
| 38 | $^t$BuO | [2-chloro-thiazol-5-yl] | (oil) | (CDCl$_3$): 0.94(d, J=7.2Hz, 6H), 1.40~2.18(m, 1H), 2.46(s, 3H), 3.99(d, J=7.2Hz, 2H), 4.89(s, 2H), 7.53(s, 1H) | T | ClCOOBu$^i$ | K$_2$CO$_3$ | CH$_3$CN |
| 39 | $^n$PrO | H | (oil) | (CDCl$_3$): 0.95(t, 3H), 1.5~2.0(m, 2H), 2.48(s, 3H), 3.25(s, 3H), 4.10 (t, 2H) | M | ClCOOPr$^n$ | K$_2$CO$_3$ | CH$_3$CN |
| 40 | $^i$PrO | H | (oil) | (CDCl$_3$): 1.25(d, 6H), 2.47(s, 3H), 3.25(s, 3H), 4.95(m, 1H) | M | ClCOOPr$^i$ | K$_2$CO$_3$ | CH$_3$CN |
| 41 | $^{sec}$Bu | H | (oil) | (CDCl$_3$): 0.7~2.8(m, 9H), 2.50(s, 3H), 3.17(s, 3H) | M | ClCOBu$^{sec}$ | pyridine | CH$_3$CN |
| 42 | MeOCH$_2$ | H | (oil) | (CDCl$_3$): 2.48(s, 3H), 3.20(s, 3H), 3.38(s, 3H), 4.23(s, 2H) | M | ClCOCH$_2$OMe | K$_2$CO$_3$ | CH$_3$CN |
| 43 | $^t$BuO | [2-chloro-thiazol-5-yl] | (oil) | (CDCl$_3$): 1.48(s, 9H), 2.46(s, 3H), 4.87(s, 2H), 7.53(s, 1H) | T | ($^t$BuOCO)$_2$O | pyridine | pyridine |
| 44 | $^{sec}$Bu | [2-chloro-thiazol-5-yl] | (oil) | (CDCl$_3$): 0.7~1.9(m, 8H), 2.15~2.80(m, 1H), 2.50(s, 3H), 4.79(s, 2H), 7.50(s, 1H) | T | ClCOBu$^{sec}$ | K$_2$CO$_3$ | CH$_3$CN |
| 45 | MeOCH$_2$ | [2-chloro-thiazol-5-yl] | (oil) | (CDCl$_3$): 2.47(s, 3H), 3.39(s, 3H), 4.25(s, 2H), 4.85(s, 2H), 7.50(s, 1H) | T | ClCOCH$_2$OMe | K$_2$CO$_3$ | CH$_3$CN |

*Starting material

EXAMPLE 1

To a suspension of sodium hydride (60% dispersion in mineral oil) in DMF (3 ml) was added a solution of 1-(2-chloro-5-thiazolylmethyl)-3,3-dimethyl-2-nitroguanidine (0.49 g) in DMF (3 ml) dropwise over 5 minutes at room temperature under stirring. After stirring for five minutes, 2.08M solution of cyanogen bromide in CH$_3$CN (1 ml) was added to the mixture over 5 minutes. After stirring for 1 hour, the reaction mixture was poured into 50 ml of water and the reaction vessel was washed with 10 ml of water. The washing was combined with the aqueous layer and precipitated pellets were obtained by filtration and recrystallized from EtOH to afford 0.334 g of 1-(2-chloro-5-thiazolylmethyl)-1-cyano-3,3-dimethyl-2-nitroguanidine (Compound No. 1) as a crystal, m.p. 152°–155° C.

NMR(CDCl$_3$)δ: 3.10(s, 6H), 4.83(s, 2H), 7.63(s, 1H)

EXAMPLE 2

A mixture of 1-(2-chloro-5-thiazolylmethyl)-1-phenoxycarbonyl-3-methyl-2-nitroguanidine (Compound No. 6), CH$_3$CN (15 ml) and pyridine (0.55 ml) was cooled to 3°–C. followed by addition of phenyl chlorocarbonate (1.7 ml) in CH$_3$CN (3 ml) below 8° C. over 2 minutes under stirring. After stirring at the same temperature for 1 hour and 25 minutes and then at room temperature for 1 hour, pyridine (0.55 ml) and phenyl chlorocarbonate (1.7 ml) was added to the mixture followed by stirring at room temperature for 1 hour and 15 minutes and at 40° C. for 2 hours. Additional phenyl chlorocarbonate (1.7 ml) was added to the mixture which was stirred for 20 minutes. To the reaction mixture was added CHCl$_3$ (30 ml) and then a mixture of conc. hydrochloric acid (2 ml) and water (8 ml). The reaction mixture was partitioned and the aqueous layer was extracted with CHCl$_3$ (20 ml×3). The combined organic layers were dried over MgSO$_4$ and concentrated in vacuo. The resulting residue was applied to column chromatography on silica gel. The column was eluted with hexane-AcOEt (3:2) to afford 0.7 g of 1-(2-chloro-5-thiazolylmethyl)-1,3-diphenoxycarbonyl-3-methyl-2-nitroguanidine (Compound No. 2) as an oil.

NMR(CDCl$_3$)δ: 3.24(s, 3H), 5.15(s, 2H), 6.7–7.7(m, 1H)

EXAMPLE 3

To a stirred solution of N-(2-chloro-5-thiazolylmethyl)-S-methyl-N'-nitro-N-n-valeroylisothiourea (1.50 g) in CHC$_3$(20 ml) was added 40% solution of methylamine-methanol (0.365 g) dropwise below −12° C. in 1 minute followed by stirring at the same temperature for 40 minutes and then at 5° C. for 10 minutes. The reaction mixture was evaporated in vacuo and the resulting residue was applied to column chromatography on silica gel. The column was eluted with CHC$_3$-EtOH (10:1) to afford 1.22 g of 1-(2-chloro-5-thiazolylmethyl)-3-methyl-2-nitro-1-n-valeroylguanidine (Compound No. 3) as a pale yellow oil. The product thus produced was crystallized by standing. m.p. 77°–79° C.

NMR(CDCl$_3$)δ: 0.9(t, J=7 Hz, 3H), 1.0-2.0(m, 4H), 2.40(t, J=7 Hz, 2H), 3.0(d, 3H), 4.88(s, 2H), 7.45(s, 1H), 9.0-10.0(br, ]H)

EXAMPLE 4

A mixture of 1-(2-chloro-5-thiazolylmethyl)-3-methyl-2-nitro-1-n-valeroylguanidine (0.73 g), pyridine (0.693 g) and CH$_2$Cl$_2$ (10 ml) was cooled to 3° C. To the cooled mixture was added acetyl chloride (0.344 g) dropwise in 1 minute under stirring. After 50 minutes, a mixed solution of conc. hydrochloric acid (2 ml) and water (1 ml) was added to the mixture followed by partition. The aqueous layer was extracted with CHCl$_3$ (10 ml ×3) and the combined organic layers were dried over MgSO$_4$ and evaporated in vacuo. The resulting residue was applied to column chromatography on silica gel. The column was eluted with CHCl$_3$-EtOH (30:1 followed by 20:1) to afford 0.35 g of 1-acetyl-3-(2-chloro-5-thiazolylmethyl)-1-methyl-2-nitro-3-n-valeroylguanidine (Compound No. 4) as a pale yellow oil.

NMR(CDCl$_3$)δ: 0.7-2.0(m, 7H), 2.0-2.8(m, 5H), 3.13(s, 3H), 4.95(br, 2H), 7.46(s, 1H)

EXAMPLE 5

To a stirred solution of N-(1--chloroethoxycarbonyl)-N-(2-chloro-5-thiazolylmethyl)-S-methyl-N'-nitroisothiourea (0.35 g) in CH$_3$CN (7 ml) was added a solution of 40% aqueous dimethylamine (0.088 g) in CH$_3$CN (3 ml) dropwise at 2° C. in 4 minutes under cooling. After stirring at the same temperature for 2 hours, precipitated crystals were obtained by filtration and dried to give 0.18 g of white crystals. To a mixture of the product and CH$_3$CN (20 ml) was added 40% aqueous solution of dimethylamine (0.04 g) dropwise at 2° C. followed by stirring at the same temperature for 30 minutes and at room temperature for 1.5 hours. The mixture was evaporated in vacuo and the resulting residue was applied to column chromatography on silica gel. The column was eluted with CHCl$_3$-EtOH (10:1) to afford 0.15 g of 1-(2-chloro-5-thiazolylmethyl)-1-dimethylaminocarbonyl-3-methyl-2-nitroguanidine (Compound No. 8) as a white crystal. m.p. 140°-141 20 C.

NMR(CDCl$_3$)δ: 2.91(d, 3H), 2.95(s, 6H), 4.93(s, 2H), 7.45(s, ]H), 9.3-9.7(br, ]H)

EXAMPLE 6

To a solution of N-(1-chloroethoxycarbonyl)-N-(2-chloro-5-thiazolylmethyl)-S-methyl-N'-nitroisothiourea (0.37 g) in CHCl$_3$ (10 ml) was added a solution of morpholine (0.091 g) in CHCl$_1$(2 ml) dropwise at 2° C. in 2 minutes. After stirring at the same temperature for 30 minutes, at room temperature for 1 hour and 15 minutes, at 30° C. for 1.5 hours and at 40° C. for 5.5 hours, morpholine (0.091 g) was added to the mixture followed by stirring at 50° C. for 1 hour and at 60° C. for 0.5 hours. After addition of additional morpholine (0.182 g) followed by stirring at 60° C. for 6 hours, the mixture was concentrated in vacuo. The resulting residue was applied to column chromatography on silica gel. The column was eluted with CHCl$_3$-EtOH (10:1) to afford 1-(2-chloro-5-thiazolylmethyl)-3-methyl-1-morpholinocarbonyl-2-nitroguanidine (Compound No. 9) as a white crystal.
m.p. 130°-131° C.

NMR(CDCl$_3$)δ: 2.92(d, 3H), 3.20-3.75(M, 8H), 4.92(s, 2H), 7.46(s, 1H), 9.2-9.7(br, 1H)

EXAMPLE 7

To a stirred mixture of S-methyl-N'-nitro-N-(npropanesulphonyl)isothiourea (2.0 g) and CH$_3$CN (20 ml) was added Et3N (0.839 g) dropwise at room temperature (exothermically). After stirring for 10 minutes, 2-chloro-5-thiazolylmethylamine (1.2 g) was added followed by reflux for 13 hours under stirring. After cooling, the mixture was concentrated in vacuo and the residue was applied to column chromatography on silica gel. The column was eluted with CHCl$_3$-EtOH (10:1) to afford an orange oil (2.2 g), to which 2N hydrochloric acid (20 ml) was added. The mixture was extracted with CHCl$_3$ (50 ml), dried over MgSO$_4$ and concentrated to afford a yellow oil (1.2 g). When standing, the product solidified. Recrystallization of a portion of the product from ETOH gave 1-(2- chloro-5-thiazolylmethyl)-2-nitro-3-(n-propanesulphonyl)guanidine (Compound No. 10) as a pale crystal. m.p. 105°-107° C.

NMR(CDCl$_3$)δ: 1.05(t, J=7.2 Hz, 3H), 1.50-2.20(m, 2H), 2.90-3.50(m,2H), 4.67(d, J=7 Hz, 2H), 6.50(br, 1H), 7.47(s, 1H), 7.90-9.20(br, 1H)

EXAMPLE 8

To a stirred solution of N-(1-chloroethoxycarbonyl)-S,N-dimethyl-N'-nitroisothiourea (6.50 g) in CHCl$_3$ (15 ml) was added a solution of 2-chloro-5-thiazolylmethylamine (3.78 g) in CHCl$_3$ (5 ml) dropwise below −20° C. over 20 minutes. After stirring at −20° C. for 30 minutes, insolubles were removed by filtration and the filtrate was concentrated in vacuo. The residue was applied to column chromatography on silica gel. The column was eluted with hexane-AcOEt (1:1) to afford 3.50 g of 1-(1-chloroethoxycarbonyl)-3-(2-chloro-5-thiazolylmethyl)-1-methyl-2-nitroguanidine (Compound No. 12) as an orange oil.

NMR(CDCl$_3$)δ: 1.72(d, J=6 Hz, 3H), 3.20(s, 3H), 4.70(s, 2H), 6.50(q, J=6 Hz, 1H), 7.50(s, 1H), 8.6-9.1(br, 1H)

EXAMPLE 9

A mixture of S,N-dimethyl-N'-nitroisothiourea (0.5 g), CH$_3$CN (6 ml) and pyridine (1 ml) was cooled to 0° C. To the cooled mixture was added benzoyl chloride (1 g) dropwise in 5 minutes under stirring. After stirring at the same temperature for 1 hour, benzoyl chloride (0.4 g) was added to the mixture which was stirred at room temperature for 1 hour. The reaction mixture was poured into 50 ml of 2N hydrochloric acid and the resulting mixture was extracted with CHCl$_3$. The extract was dried over MgSO$_4$ and evaporated in vacuo. The resulting residue was applied to column chromatography on silica gel. The column was eluted with hexane-AcOEt (5:1) to afford 0.71 g of crude N-benzoyl-S,N-dimethyl-N'-nitroisothiourea as an oil. To the solution of the product (0.636 g) in CH$_3$CN (4 ml) was added a solution of 2-chloro-5-thiazolylmethylamine (0.37 g) in CH$_3$CN (2 ml) dropwise at 0° C. over 5 minutes. After stirring at the same temperature for 25 minutes, precipitates were collected by filtration and the product was applied to column chromatography on silica gel. The column was eluted with CH$_2$Cl$_2$-MeOH (20:1) to afford 0.344 g of 1-benzoyl-3-(2-chloro-5-thiazolylmethyl)-1-methyl-2-nitroguanidine (Compound No. 15) as a crystal, m.p. 170°-172° C.

NMR(DMSO-d$_6$)δ: 3.18(s, 3H), 4.45(s, 2H), 7.20-7.66(m, 6H), 9.68 (brs, 1H)

EXAMPLE 10

To a solution of 1-(2-chloro-5-thiazolylmethyl)-3,3-dimethyl-2-nitroguanidine (0.300 g) in an aqueous NaOH solution (NaOH (0.319 g) and water (10 ml)) were added CH$_2$Cl$_2$ (10 ml) and 4-dimethylaminopyridine (0.013 g). To the mixture was added methanesulphonyl chloride (0.391 g) dropwise at room temperature under stirring. After stirring for 30 minutes, the mixture was partitioned. The organic layer was dried over MgSO, and concentrated in vacuo. The resulting residue was applied to column chromatography on silica gel. The column was eluted with hexane-AcOEt (1:1) to afford 0.160 g of 1-(2-chloro-5-thiazolylmethyl)-3,3-dimethyl-1-methanesulphonyl-2-nitroguanidine (Compound No. 28) as a pale yellow crystal, m.p. 82°–86° C.

NMR(CDCl$_3$)δ: 3.07(s, 6H), 3.18(s, 3H), 4.76(s, 2H), 7.54(s, 1H)

EXAMPLE 11

To a solution of N-(2-chloro-5-thiazolylmethyl)-S-methyl-N'-nitro-N-propionylisothiourea (310 mg) in toluene (5 ml) was added 40% methylamine-methanol solution (75 mg) below −10° C. and the mixture was stirred at the same temperature for 3 hours. After addition of 2N hydrochloric acid (5 ml) under ice-cooling, the mixture was extracted with AcOEt (10 ml). The organic layer was washed with an aqueous saturated sodium bicarbonate solution, dried over MgSO$_4$ and concentrated in vacuo. The resulting residue was applied to column chromatography on silica gel. The column was eluted with AcOEt. The fractions containing the desired compound were concentrated and the residue was dissolved in toluene. Crystallization by addition of n-hexane gave 120 mg of 1-(2-chloro-5-thiazolylmethyl)-3-methyl-2-nitro-1-propionylguanidine (Compound No. 32) as a white crystal, m.p. 89°–90° C.

NMR(CDCl$_3$)δ: 1.19(t, J=7.2 Hz, 3H), 2.46(q, J=7.2 Hz, 2H), 2.99(d, J=5.4 Hz, 3H), 4.90(s, 2H), 7.47(s, 1H)

EXAMPLE 12

To a solution of N-iso-butyroyl-N-(2-chloro-5-thiazolylmethyl)-S-methyl-N'-nitroisothiourea (560 mg) in dichloromethane (5 ml) was added 40% methylamine-methanol solution (129 mg) dropwise below −11° C. and the mixture was stirred at the same temperature for 1 hour. To the mixture was added 40% methylamine-methanol solution (64 mg) dropwise below −11° C. and the mixture was stirred at the same temperature for 5.5 hours. After addition of 2N hydrochloric acid (10 ml) under ice-cooling, the mixture was extracted with toluene (5 ml). The organic layer was washed with an aqueous saturated sodium bicarbonate solution, dried over MgSO$_4$ and concentrated in vacuo. The residue was dissolved in toluene. Crystallization by addition of n-hexane gave 190 mg of 1-iso-butyroyl-1-(2-chloro-5-thiazolylmethyl)-3-methyl-2-nitroguanidine (Compound No. 34) as a white crystal, m.p. 101°–104° C.

NMR(CDCl$_3$)δ: 1.19(d, J=6.6 Hz, 6H), 2.4–2.9(m, ]H), 2.98(d, J=5.4 Hz, 3H), 4.88(s, 2H), 7.47(s, 1H)

EXAMPLE 13

To a mixture of 1-(2-chloro-5-thiazolylmethyl)-3,3-dimethyl-2-nitroguanidine (200 mg), K$_2$CO$_3$ (420 mg) and CH$_3$CN (13 ml) was added phenyl chlorothionoformate (260 mg) dropwise in 3 minutes at 3° C. under stirring. After stirring at room temperature for 4 hours, water (10 ml) was added to the mixture which was extracted with CHCl$_3$ (20 ml). The organic layer was dried over MgSO$_4$ and evaporated in vacuo. The residue was crystallized from AcOEt-Et$_2$O to afford 230 mg of 1-(2-chloro-5-thiazolylmethyl)-3,3-dimethyl-2-nitro-1-phenoxythiocarbonylguanidine (Compound No. 44) as a white crystal, m.p. 161°–162° C.

NMR(CDCl$_3$)δ: 2.91(s, 3H), 3.14(s, 3H), 4.81(d, J=15.6 Hz, 1H), 5.54(d, J=15.6 Hz, ]H), 6.9–7.7(m, 6H)

EXAMPLE 14

To a solution of N-(2-chloro-5-thiazolylmethyl)-N-methoxycarbonyl-S-methyl-N'-nitroisothiourea (500 mg) in MeOH (5 ml) was added 40% methylamine-methanol solution (120 mg) dropwise below −10° C. and the mixture was stirred at the same temperature. Precipitated crystals were collected by filtration and dried to afford 230 mg of 1-(2-chloro-5-thiazolylmethyl)-1-methoxycarbonyl-3-methyl-2-nitroguanidine (Compound No. 19) as a white crystal. The filtrate was concentrated to leave the residue to which MeOH (3 ml) was added. The product (Compound No. 19, 140 mg) was obtained after drying. The properties, i.e. m.p., NMR and IR, of the product are identical with those of the compound prepared according to Example 3.

EXAMPLE 18

The procedure of Example 11 was repeated replacing the N-(2-chloro-5-thiazolylmethyl)-S-methyl-N'-nitro-N-propionylisothiourea and toluene with N-t-butoxycarbonyl-N-(2-chloro-5-thiazolylmethyl)-S-methyl-N'-nitroisothiourea and AcOEt to obtain 1-(t-butoxycarbonyl)-I-(2-chloro-5-thiazolylmethyl)-3-methyl-2-nitroguanidine (Compound No. 54) as a pale yellow oil.

NMR(CDCl$_3$)δ: 1.53(s, 9H), 2.98(d, J=5.4 Hz, 3H), 4.93(s, 2H), 7.51(s, 1H), 9.80(br, 1H)

The following compounds listed in Table 5 below were prepared according to the procedures of Examples 1–15 or the analogues of the present invention. The compounds listed in Table 5 include those prepared in the above-mentioned Examples.

TABLE 5

$$R^1-CH_2-N\underset{R^3-N}{\overset{R^2}{\underset{R^4}{|}}}C=N-NO_2$$

| Compound No. | R¹ | R² | R³ | R⁴ | mp(°C.) | Preparation Method (Corres. to Ex. No.) | NMR (solvent)δ: |
|---|---|---|---|---|---|---|---|
| 1 | 2-chloro-5-thiazolyl-CH= (Cl-C(=N-)-S-C(Me)=) | —CN | Me | Me | 152–155 | 1 | (CDCl₃): 3.10(s, 6H), 4.83(s, 2H), 7.63(s, 1H) |
| 2 | (same) | COOPh | COOPh | Me | (oil) | 2 | (CDCl₃): 3.24(s, 3H), 5.15(s, 2H), 6.7~7.7 (m, 11H) |
| 3 | (same) | ⁿBuCO | H | Me | 77–79 | 3 | (CDCl₃);0.9(t, J=7Hz, 3H), 1.0~2.0(m, 4H), 2.40 (t, J=7Hz, 2H), 3.0(d, 3H), 4.88(s, 2H), 7.45(s, 1H), 9.0~10.0(br, 1H) |
| 4 | (same) | ⁿBuCO | Ac | Me | (oil) | 4 | (CDCl₃): 0.7~2.0(m, 7H), 2.0~2.8(m, 7H), 3.13(s, 3H), 4.95(br, 2H), 7.46 (s, 1H) |
| 5 | (same) | PhCO | H | Me | 155–157 | 3 | (CDCl₃): 2.65(d, 3H), 5.15(s, 2H), 7.3~7.9(m, 6H), 9.3~9.7(br, 1H) |
| 6 | (same) | PhOCO | H | Me | 106–108 | 3 | (CDCl₃): 3.20(d, 3H), 5.05(s, 2H), 6.5~7.8(m, 6H), 9.5~10.0(br, 1H) |
| 7 | (same) | MeCHClOCO | H | Me | 115–117 | 3 | (CDCl₃): 1.85(d, J=6Hz, 3H), 3.10(d, 3H), 4.95(d, 2H), 6.55(q, J=6Hz, 1H), 7.53(s, 1H), 9.6~10.0 (br, 1H) |
| 8 | (same) | Me₂NCO | H | Me | 140–141 | 5 | (CDCl₃): 2.91(d, 3H), 2.95(s, 6H), 4.93(s, 2H), 7.45(s, 1H), 9.3~9.7 (br, 1H)) |
| 9 | (same) | morpholino-CO (O(CH₂CH₂)₂N-CO) | H | Me | 130–131 | 6 | (CDCl₃): 2.92(d, 3H), 3.20~3.75(m, 8H), 4.92 (s, 2H), 7.46(s, 1H), 9.2~ 9.7(br, 1H) |
| 10 | (same) | H | ⁿPrSO₂ | H | 105–107 | 7 | (CDCl₃): 1.05(t, J=7.2Hz, 3H), 1.50~2.20(m, 2H), 2.90~3.50(m, 2H), 4.67(d, J=7Hz, 2H), 6.50(br, 1H), 7.47(s, 1H), 7.90~9.20 (br, 1H) |
| 11 | (same) | pyrrolidino-CO | H | Me | 151–152 | 6 | (CDCl₃): 1.50~2.30(m, 4H), 2.90(d, 3H), 3.2~3.6 (m, 4H), 4.97(s, 2H), 7.48 (s, 1H), 9.50~9.90(br, 1H) |

TABLE 5-continued $$R^1-CH_2-\underset{R^2}{N}-\underset{}{\overset{}{C}}=N-NO_2$$
$$\underset{R^4}{\overset{R^3-N}{|}}$$

| Compound No. | R¹ | R² | R³ | R⁴ | mp(°C.) | Preparation Method (Corres. to Ex. No.) | NMR (solvent)δ: |
|---|---|---|---|---|---|---|---|
| 12 | 2-chloro-5-thiazolyl | H | COOCHMeCl | Me | (oil) | 8 | (CDCl₃): 1.72(d, J=6Hz, 3H), 3.20(s, 3H), 4.70(s, 2H), 6.50(q, J=6Hz, 1H), 7.50(s, 1H), 8.6∼9.1(br, 1H) |
| 13 | 2-chloro-5-thiazolyl | H | COOPh | Me | 110–111 | 8 | (CDCl₃): 3.36(s, 3H), 4.70(d, J=4Hz, 2H), 7.0∼7.6(m, 6H), 9.0(br, 1H) |
| 14 | 2-chloro-5-thiazolyl | H | MeSO₂ | Me | 138–139 | 8 | (CDCl₃): 3.17(s, 3H), 3.18(s, 3H), 4.88(d, J=6 Hz, 2H), 7.53(s, 1H), 9.0 (br, 1H) |
| 15 | 2-chloro-5-thiazolyl | H | PhCO | Me | 170–172 | 9 | (DMSO-d₆): 3.18(s, 3H), 4.45(s, 2H), 7.20∼7.66 (m, 6H), 9.68(br s, 1H) |
| 16 | 2-chloro-5-thiazolyl | H | Me₂NCO | Me | 110–111 | 5 | (CDCl₃): 3.0(s, 6H), 3.15(s, 3H), 4.60(d, 2H), 7.44(s, 1H), 8.3∼8.7(br, 1H) |
| 17 | 2-chloro-5-thiazolyl | H | morpholino-NCO | Me | 72–74 | 6 | (CDCl₃): 3.18(s, 3H), 3.0∼3.9(m, 8H), 4.57(s, 2H), 7.50(s, 1H), 8.5∼9.1 (br, 1H) |
| 18 | 2-chloro-5-thiazolyl | H | MeOCO | Me | 78–80 | 8 | (CDCl₃): 3.22(s, 3H), 3.85(s, 3H), 4.69(d, J=5 Hz, 2H), 7.51(s, 1H), 9.14(br, 1H) |
| 19 | 2-chloro-5-thiazolyl | MeOCO | H | Me | 134–135 | 3 | (CDCl₃): 2.97(s, 3H), 3.88(s, 3H), 4.98(s, 2H), 7.52(s, 1H), 9.80(br, 1H) |
| 20 | 2-chloro-5-thiazolyl | H | PhCH₂CO | Me | (oil) | 8 | (CDCl₃): 3.16(s, 3H), 3.83(s, 2H), 4.38(d, J=6 Hz, 2H), 7.13–7.47(m, 6H), 8.75(br s, 1H) |
| 21 | 2-chloro-5-thiazolyl | PhCH₂CO | H | Me | 155–158 | 3 | (CDCl₃): 2.69(d, J=5Hz, 3H), 3.87(s, 2H), 4.81(s, 2H), 7.13∼7.43(m, 5H), 7.40(s, 1H), 9.0∼9.7 (br s, 1H) |
| 22 | 2-chloro-5-thiazolyl | H | 2-thienyl-CO | Me | 174–176.5 | 8 | (DMSO-d₆): 3.17(s, 3H), 4.55(s, 2H), 7.03(t, J=4 Hz, 1H), 7.43(dd, J=4&1Hz, 1H), 7.57(s, 1H), 7.85(dd, J=4&1Hz, 1H) |
| 23 | 2-chloro-5-thiazolyl | 2-thienyl-CO | H | Me | 160–162 | 3 | (CDCl₃): 2.75(d, J=6Hz, 3 H), 5.13(s, 2H), 7.0∼7.2 (m, 1H), 7.45∼7.75(m, 3H), 9.55(br s, 1H) |

TABLE 5-continued $$R^1-CH_2-N\begin{matrix}R^2\\|\\\\|\\R^3\end{matrix}\ C=N-NO_2,\ R^3-N-R^4$$

| Compound No. | R[1] | R[2] | R[3] | R[4] | mp(°C.) | Preparation Method (Corres. to Ex. No.) | NMR (solvent)δ: |
|---|---|---|---|---|---|---|---|
| 24 | 2-chlorothiazol-5-yl | PhCO | PhCO | Me | 115–116 | 2 | (CDCl$_3$): 2.60(s, 3H), 4.40(s, 2H), 7.0–7.8 (m, 11H), |
| 25 | 2-chloropyridin-5-yl | H | PhCH$_2$OCO | Me | 79–80 | 8 | (CDCl$_3$): 3.20(s, 3H), 4.47(br s, 2H), 5.22(s, 2H) 7.10–7.45(m, 6H), 7.59(dd, J=8&2Hz, 1H), 8.27(d, J=2Hz, 1H), 9.37 (br, 1H) |
| 26 | 2-chlorothiazol-5-yl | H | PhCH$_2$OCO | Me | (oil) | 8 | (CDCl$_3$): 3.21(s, 3H), 4.58(d, J=5Hz, 2H), 5.23 (s, 2H), 7.38(s, 6H), 9.16 (br, 1H) |
| 27 | 2-chlorothiazol-5-yl | PhCH$_2$OCO | H | Me | (oil) | 3 | (CDCl$_3$): 2.89(d, J=5Hz, 3H), 4.95(s, 2H), 5.25(s, 2H), 7.37(s, 6H), 9.76(br, 1H) |
| 28 | 2-chlorothiazol-5-yl | MeSO$_2$ | Me | Me | 82–86 | 10 | (CDCl$_3$): 3.07(s, 6H), 3.18(s, 3H), 4.76(s, 2H), 7.54(s, 1H) |
| 29 | 2-chlorothiazol-5-yl | H | $^i$PrCO | Me | 91–92 | 8 | (CDCl$_3$): 1.15(d, 6H), 2.5–3.1(m, 1H), 3.20(s, 3H), 4.62 (s, 2H), 7.49(s, 1H), 8.5–9.1 (br, 1H) |
| 30 | 2-chlorothiazol-5-yl | H | $^t$Bu-C$_6$H$_4$-CO | Me | 163–165 | 8 | (CDCl$_3$): 1.32(s, 9H), 3.30 (s, 3H), 4.45(br d, 2H), 7.2–7.70(m, 5H), 8.1–8.5(m, 1H) |
| 31 | 2-chlorothiazol-5-yl | H | Cl$_3$CS | Me | 117–121 | 8 | (CDCl$_3$): 3.66(s, 3H), 4.68 (d, J=6Hz, 2H), 7.47(s, 1H) 7.2–7.8(br, 1H) |
| 32 | 2-chlorothiazol-5-yl | EtCO | H | Me | 89–90 | 11 | (CDCl$_3$): 1.19(t, J=7.2Hz, 3H), 2.46(q, J=7.2Hz, 2H), 2.99(d, J=5.4Hz, 3H), 4.90 (s, 2H), 7.47(s, 1H) |
| 33 | 2-chlorothiazol-5-yl | $^n$PrCO | H | Me | 102–106 | 11 | (CDCl$_3$): 0.95(m, 3H), 1.35–2.00(m, 2H), 2.15–2.63(m, 2H), 2.98(d, J=5.4Hz, 3H), 4.88(s, 2H), 7.47(s, 1H), 8.5–10(br, 1H) |
| 34 | 2-chlorothiazol-5-yl | $^i$PrCO | H | Me | 101–104 | 12 | (CDCl$_3$): 1.16(d, J=6.6Hz, 6H), 2.4–2.9(m, 1H), 2.98 (d, J=5.4Hz, 3H), 4.88(s, 2H)7.47(s, 1H) |
| 35 | 2-chlorothiazol-5-yl | $^i$BuCO | H | Me | 95–98 | 12 | (CDCl$_3$): 0.95(d, J=6Hz, 6H), 1.55–1.75(m, 1H), 2.15–2.38(m, 2H), 2.98(d, J=5.4Hz, 3H), 4.88(s, 2H), 7.47(s, 1H) |

TABLE 5-continued

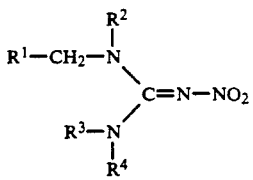

| Compound No. | R¹ | R² | R³ | R⁴ | mp(°C.) | Preparation Method (Corres. to Ex. No.) | NMR (solvent)δ: |
|---|---|---|---|---|---|---|---|
| 36 | 2-chloro-thiazol-5-yl | H | EtCO | Me | 82-83 | 8 | (CDCl$_3$): 1.13(t, 3H), 2.45 (q, 2H), 3.18(s, 3H), 4.62 (br s, 2H), 7.48(s, 1H), 8.9~9.2(br, 1H) |
| 37 | 2-chloro-thiazol-5-yl | H | $^n$PrCO | Me | 70-71 | 8 | (CDCl$_3$): 0.90(t, 3H), 1.62 (m, 2H), 2.40(t, 2H), 3.15(s, 3H), 4.63(s, 2H), 7.50(s, 1H) 8.9~9.2(br, 1H) |
| 38 | 2-chloro-thiazol-5-yl | H | $^n$BuCO | Me | 91-92 | 8 | (CDCl$_3$): 0.7~1.85(m, 7H), 2.2~2.6(m, 2H), 3.20(s, 3H), 4.62(d, 1H), 7.50(s, 1H), 8.9~9.2(br, 1H) |
| 39 | 2-chloro-thiazol-5-yl | H | $^i$BuCO | Me | 84-85 | 8 | (CDCl$_3$): 0.93(d, 6H), 2.23 (br s, 3H), 3.15(s, 3H), 4.62 (s, 2H), 7.48(s, 1H), 8.6~9.2 (br, 1H) |
| 40 | 2-chloro-thiazol-5-yl | H | COOEt | Me | 45-47 | 8 | (CDCl$_3$): 1.30(t, 3H), 3.20 (s, 3H), 4.25(q, 2H), 4.65 (s, 2H), 7.50(s, 1H), 8.8~9.3 (br, 1H) |
| 41 | 2-chloro-thiazol-5-yl | H | COOBu$^n$ | Me | 39-40 | 8 | (CDCl$_3$): 0.8~2.0(m, 7H), 3.20(s, 3H), 4.20(t, 2H), 4.65(s, 2H), 7.48(s, 1H), 8.9~9.3(br, 1H) |
| 42 | 2-chloro-thiazol-5-yl | H | COOBu$^i$ | Me | 66-67 | 8 | (CDCl$_3$): 0.95(d, 6H), 1.70~2.25(m, 1H), 3.23(s, 3H), 4.00(d, 2H), 4.65(s, 2H), 7.50(s, 1H), 9.0~9.4(br, 1H) |
| 43 | 2-chloro-thiazol-5-yl | H | COOBu$^t$ | Me | 102-103 | 8 | (CDCl$_3$): 1.50(s, 9H), 3.18 (s, 3H), 4.65(d, 2H), 7.50 (s, 1H), 9.1~9.3(br, 1H) |
| 44 | 2-chloro-thiazol-5-yl | PhOCS | Me | Me | 161-162 | 13 | (CDCl$_3$): 2.91(s, 3H), 3.14 (s, 3H), 4.81(d, J=15.6Hz, 1H), 5.54(d, J=15.6Hz, 1H), 6.9~7.7(m, 6H) |
| 45 | 2-chloro-thiazol-5-yl | EtOCO | H | Me | 111-112 | 12 | (CDCl$_3$): 1.36(t, J=7.2Hz, 3H), 2.97(d, J=6Hz, 3H), 4.35 (q, J=7.2Hz, 2H), 4.99(s, 2H) 7.54(s, 1H), 9.85(br, 1H) |
| 46 | 2-chloro-thiazol-5-yl | $^n$PrOCO | H | Me | 96-97.5 | 12 | (CDCl$_3$): 0.97(t, J=7.2Hz, 3H), 1.43~2.00(m, 2H), 2.97 (d, J=5.4Hz, 3H), 4.23(t, J=7.2Hz, 2H), 4.98(s, 2H), 7.53 (s, 1H), 9.82(br, 1H) |
| 47 | 2-chloro-thiazol-5-yl | $^i$PrOCO | H | Me | 111-115 | 12 | (CDCl$_3$): 1.31(d, J=7.2Hz, 6H), 2.97(d, J=5.4Hz, 3H), 4.80~5.33(m, 1H), 4.99(s, 2H), 7.52(s, 1H), 9.82(br, 1H) |

TABLE 5-continued $$R^1-CH_2-N(R^2)-C(=N-NO_2)-N(R^3)(R^4)$$

| Compound No. | R¹ | R² | R³ | R⁴ | mp(°C.) | Preparation Method (Corres. to Ex. No.) | NMR (solvent)δ: |
|---|---|---|---|---|---|---|---|
| 48 | 2-chloro-thiazol-5-yl | ⁿBuOCO | H | Me | ( ) | 12 | (CDCl₃): 0.7∼1.1(m, 3H), 1.1∼1.9(m, 4H), 2.98(d, J=5.4Hz, 3H), 3.90∼4.45(m, 2H) 4.97(s, 2H), 7.50(s, 1H), 9.82(br, NH) |
| 49 | 2-chloro-thiazol-5-yl | ⁱBuOCO | H | Me | ( ) | 12 | (CDCl₃): 0.95(d, J=6.6Hz, 6H), 1.6∼2.3(m, 1H), 2.98 (d, J=5.4Hz, 3H), 4.50(d, J=6.6Hz, 2H), 4.98(s, 2H), 7.51 (s, 1H), 9.80(br, 1H) |
| 50 | 2-chloro-thiazol-5-yl | H | COOPrⁿ | Me | 91–92 | 8 | (CDCl₃): 0.97(t, 3H), 1.4∼2.0(m, 2H), 3.25(s, 3H), 4.21 (t, 2H), 4.62(br s, 2H), 7.52 (s, 1H), 9.0∼9.6(br, 1H) |
| 51 | 2-chloro-thiazol-5-yl | H | COOPrⁱ | Me | 94–95 | 8 | (CDCl₃): 1.30(d, 6H), 3.20 (s, 3H), 4.65(br d, 2H), 4.75∼5.25(m, 1H), 7.50(s, 1H), 9.0∼9.4(br, 1H) |
| 52 | 2-chloro-thiazol-5-yl | H | COBuˢᵉᶜ | Me | 114–115 | 8 | (CDCl₃): 0.89(t, 3H), 1.15 (d, 3H), 1.3∼1.8(m, 2H), 2.3∼2.8(m, 1H), 3.22(s, 3H), 4.65(s, 2H), 7.48(s, 1H), 8.7∼7.3(br, 1H) |
| 53 | 2-chloro-thiazol-5-yl | H | MeOCH₂CO | Me | 78–80 | 8 | (CDCl₃): 3.10(s, 3H), 3.30 (s, 3H), 4.15(s, 2H), 4.65 (s, 2H), 7.50(s, 1H), 8.7∼9.3 (br, 1H) |
| 54 | 2-chloro-thiazol-5-yl | ᵗBuOCO | H | Me | (oil) | 15 | (CDCl₃): 1.53(s, 9H), 2.98 (d, J=5.4Hz, 3H), 4.93(s, 2H) 7.51(s, 1H), 9.80(br, 1H) |
| 55 | 2-chloro-thiazol-5-yl | ˢᵉᶜBuCO | H | Me | 146–147.5 | 15 | (CDCl₃): 0.73∼1.90(m, 8H), 2.20∼2.72(m, 1H), 2.90(br s, 3H), 4.77(s, 2H), 7.50(s, 1H), 8.75(br, 1H) |
| 56 | 2-chloro-pyridin-5-yl | H | ⁱPrCO | H | 127–128.5 | 9 | |
| 57 | 2-chloro-pyridin-5-yl | H | MeOCO | H | 121.5–124 | 8 | |

EXAMPLE 16

An emulsifiable concentrate was prepared by well-mixing Compound No. 3 (20 wt %), xylene (75 wt %) and polyoxyethylene glycol ether (Nonipol 85 ™, 5 wt %).

EXAMPLE 17

Wettable powders were prepared by well-mixing Compound No. 5 (30 wt %), sodium ligninsulfonate (5 wt %), polyoxyethylene glycol ether (Nonipol 85 ™, 5 wt %), white carbon (30 wt %) and clay (30 wt %).

EXAMPLE 18

A dust was prepared by well-mixing Compound No. 6 (3 wt %), white carbon (3 wt %) and clay (94 wt %).

EXAMPLE 19

Granules were prepared by thoroughly pulverizing and well-mixing Compound No. 7 (10 wt %), sodium ligninsulfonate (5 wt %) and clay (85 wt %), kneading the mixture with water, granulating and drying the resultant.

EXAMPLE 20

A pesticidal dust was prepared by well-mixing Compound No. 18 (0.275 wt %), cartap (2.2 wt %), white carbon (0.5 wt %) and clay (97.025 wt %).

EXAMPLE 21

A pesticidal-fungicidal dust was prepared by well-mixing Compound No. 19 (0.275 wt %), validamycin (0.33 wt %), white carbon (0.5 wt %) and clay (98.895 wt %).

The following references, which are referred to for their disclosures at various points in this application, are incorporated herein by reference.
1. European Patent Application Laid Open No. 0,375,907 A1.
2. European Patent Application Laid Open No. 0,376,279 A2.
3. Survey of Organic Synthesis, Wiley-Interscience (1970), Chapter 8.
4. SHIN JIKENKAGAKU KOZA (New Experimental Chemistry Handbook), Maruzen Publishing Co., Ltd., Japan, Vol. 14-III, pp. 1332-1399.
5. Organic Functional Group Preparations, Academic Press, Vol.1, Chapter 13 (1968), and Vol.3, Chapter 10 (1972).
6. Japanese Patent Laid Open No. 171/1990.
7. Japanese Patent Laid Open No. 333721/1989.
8. Organic Functional Group Preparations, Academic Press, Vol.1, Chapter 6 (1968).
9. SHIN JIKENKAGAKU KOZA (New Experimental Chemistry Handbook), Maruzen Publishing Co., Ltd., Japan, Vol. 14-I, pp. 307-450, and Vol. 14-II, pp. 1104-1133.
10. Rodd's Chemistry of Carbon Compounds, Vol. 1, Part c, pp. 341-353.
11. Chemical Reviews, 51, 301 (1952).

What is claimed is:

1. A compound of the formula:

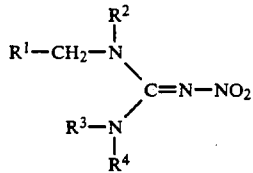

[I]

wherein $R^1$ is a heterocyclic group having a single or fused ring with 5 to 8 ring members in each ring and having from 1 to 5 heteroatoms in each ring independently selected from the group consisting of oxygen, nitrogen, and sulfur, wherein said heterocyclic group may optionally be substituted with 1 to 5 substituents which may be the same or different selected from the group consisting of $C_{1-15}$ alkyl optionally substituted with 1 to 5 substituents selected from the group consisting of halogen, hydroxyl, $C_{1-4}$ alkoxy, and $C_{1-4}$ alkylthio; $C_{3-10}$ cycloalkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{2-10}$ alkenyl optionally substituted with 1 to 5 substituents selected from the group consisting of halogen, hydroxyl, $C_{1-4}$ alkoxy, and $C_{1-4}$ alkylthio; $C_{2-10}$ alkynyl optionally substituted with 1 to 5 substituents selected from the group consisting of halogen, hydroxyl, $C_{1-4}$ alkoxy, and $C_{1-4}$ alkylthio; $C_{3-10}$ cycloalkenyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{6-10}$ aryl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{7-10}$ aralkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; nitro; hydroxyl; mercapto; oxo; thioxo; cyano; carbamoyl; carboxyl; $C_{1-4}$ alkoxycarbonyl; sulfo; halogen; $C_{1-4}$ alkoxy optionally substituted with 1 to 5 substituents selected from the group consisting halogen, hydroxyl, $C_{1-4}$ alkoxy, and $C_{1-4}$ alkylthio; $C_{6-10}$ aryloxy optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{1-4}$ alkylthio optionally substituted with 1 to 5 substituents selected from the group consisting of halogen, hydroxyl, $C_{1-4}$ alkoxy, and $C_{1-4}$ alkylthio; $C_{6-10}$ arylthio optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{1-4}$ alkylsulfinyl optionally substituted with 1 to 5 substituents selected from the group consisting of halogen, hydroxyl, $C_{1-4}$ alkoxy, and $C_{1-4}$ alkylthio; $C_{6-10}$ arylsulfinyl optionally substituted with 1 to 5 substitutents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{1-4}$ alkylsulfonyl optionally substituted with 1 to 5 substituents selected from the group consisting of halogen, hydroxyl, $C_{1-4}$ alkoxy, and $C_{1-4}$ alkylthio; $C_{6-10}$ arylsulfonyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; amine optionally substituted with 1 to 2 substituents selected from the group consisting of halogen, hydroxyl, $C_{1-4}$ alkoxy, and $C_{1-4}$ alkylthio; $C_{2-6}$ acylamino; mono- or di-$C_{1-4}$ alkylamino optionally substituted with 1 to 5 substituents selected from the group consisting of halogen, hydroxyl, $C_{1-4}$ alkoxy, and $C_{1-4}$ alkylthio; $C_{3-6}$ cycloalkylamino optionally substituted with 1 to 5 substituents selected from the group consisting of halogen, hydroxyl, $C_{1-4}$ alkoxy, and $C_{1-4}$ alkylthio; $C_{6-10}$ arylamino optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{2-4}$ acyl; $C_{6-10}$ arylcarbonyl; and 5 to 6 membered heterocyclic containing from 1 to 4 heteroatoms selected from the group consisting of oxygen, sulfur, and nitrogen optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio;

$R^2$ is cyano;

—CO—$OR^6$ wherein $R^6$ is a hydrocarbon group selected from the group consisting of $C_{1-15}$ alkyl optionally substituted with 1 to 5 substituents selected from the group consisting of halogen, hydroxyl, $C_{1-4}$ alkoxy, and $C_{1-4}$ alkylthio; $C_{3-10}$ cycloalkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkyl, $C_{1-4}$ alkylthio, and phenylthio; $C_{2-10}$ alkenyl optionally substituted with 1 to 5 substituents selected from the group consisting of halogen, hydroxyl, $C_{1-4}$ alkoxy, and $C_{1-4}$ alkylthio; $C_{2-10}$ alkynyl optionally substituted with 1 to 5 substituents selected from the group consisting of halogen, hydroxyl, $C_{1-4}$ alkoxy, and $C_{1-4}$ alkylthio; $C_{3-10}$ cycloalkenyl optionally substituted with 1 to 5 substitutents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{6-10}$ aryl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; and $C_{7-10}$ aralkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkythio, and phenylthio; or $R^6$ is a heterocyclic group as defined for $R^1$;

or —CO—$NR^7R^8$ wherein $R^7$ and $R^8$, which are the same or different, are each independently hydrogen, a hydrocarbon group selected from the group consisting of $C_{1-15}$ alkyl optionally substituted with 1 to 5 substituents selected from the group consisting of halogen, hydroxyl, $C_{1-4}$ alkoxy, and $C_{1-4}$ alkylthio; $C_{3-10}$ cycloalkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{2-10}$ alkenyl optionally substituted with 1 to 5 substituents selected from the group consisting of halogen, hydroxyl, $C_{1-4}$ alkoxy, and $C_{1-4}$ alkylthio; $C_{2-10}$ alkynyl optionally substituted with 1 to 5 substituents selected from the group consisting of halogen, hydroxyl, $C_{1-4}$ alkoxy, and $C_{1-4}$ alkylthio; $C_{3-10}$ cycloalkenyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{6-10}$ aryl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; and $C_{7-10}$ aralkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; or a heterocyclic group as defined for $R^1$;

or $R^7$ or $R^8$, taken together with the nitrogen atom to which they are attached are a cyclic amino group selected from the group consisting of aziridino, azetidino, pyrrolidino, piperazino, piperidino, morpholino, and thiomorpholino which may optionally be substituted with 1 to 4 $C_{1-4}$ alkyl groups;

$R^3$ is hydrogen, a hydrocarbon group except for one substituted with an oxo group at the binding site selected from the group consisting of $C_{1-15}$ alkyl optionally substituted with 1 to 5 substituents selected from the group consisting of halogen, hydroxyl, $C_{1-4}$ alkoxy, and $C_{1-4}$ alkylthio; $C_{3-10}$ cycloalkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{2-10}$ alkenyl optionally substituted with 1 to 5 substituents selected from the group consisting of halogen, hydroxyl, $C_{1-4}$ alkoxy, and $C_{1-4}$ alkylthio; $C_{2-10}$ alkynyl optionally substituted with 1 to 5 substituents selected from the group consisting of halogen, hydroxyl, $C_{1-4}$ alkoxy, and $C_{1-4}$ alkylthio; $C_{3-10}$ cycloalkenyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{6-10}$ aryl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; and $C_{7-10}$ aralkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio;

—$S(O)_n$—$R^{13}$ wherein n is an integer selected from the group consisting of 0, 1, and 2 and $R^{13}$ is selected from the group consisting of a heterocyclic group as defined for $R^1$; $C_{1-15}$ alkyl optionally substituted with 1 to 5 substituents selected from the group consisting of halogen, hydroxy, $C_{1-4}$ alkoxy, and $C_{1-4}$ alkylthio; $C_{3-10}$ cycloalkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{2-10}$ alkenyl optionally substituted with 1 and 5 substituents selected from the group consisting of halogen, hydroxyl, $C_{1-4}$ alkoxy, and $C_{1-4}$ alkylthio; $C_{2-10}$ alkynyl optionally substituted with 1 to 5 substituents selected from the group consisting of halogen, hydroxyl, $C_{1-4}$ alkoxy, and $C_{1-4}$ alkylthio; $C_{3-10}$ cycloalkenyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{6-10}$ aryl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; and $C_{7-10}$ aralkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio;

—P(=O)$R^{14}R^{15}$ wherein $R^{14}$ and $R^{15}$ are each independently a heterocyclic group as defined for $R^1$; $C_{1-15}$ alkyl optionally substituted with 1 to 5 substituents selected from the group consisting of halogen, hydroxyl, $C_{1-4}$ alkoxy, and $C_{1-4}$ alkylthio; $C_{3-10}$ cycloalkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{2-10}$ alkenyl optionally substituted with 1 to 5 substituents selected from the group consisting of halogen, hydroxyl, $C_{1-4}$ alkoxy, and $C_{1-4}$ alkylthio; $C_{2-10}$ alkynyl optionally substituted with 1 to 5 substituents selected from the group consisting of halogen, hydroxyl, $C_{1-4}$ alkoxy, and $C_{1-4}$ alkylthio; $C_{3-10}$ cycloalkenyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{6-10}$ aryl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; and $C_{7-10}$ aralkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio;

cyano;

—CO—$R^9$ wherein $R^9$ is hydrogen, a hydrocarbon group selected from the group consisting of $C_{1-15}$ alkyl optionally substituted with 1 to 5 substituents selected from the group consisting of halogen, hydroxyl, $C_{1-4}$ alkoxy, and $C_{1-4}$ alkylthio; $C_{3-10}$ cycloalkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{2-10}$ alkenyl optionally substituted with 1 to 5 substituents selected from the group consisting of halogen, substituted with 1 to 5 substituents selected from the group consisting of halogen, hydroxyl, $C_{1-4}$ alkoxy, and $C_{1-4}$ alkylthio; $C_{3-10}$ cycloalkenyl optionally substituted with 1 to 5 substituents consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; $C_{6-10}$ aryl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; and $C_{7-10}$ aralkyl optionally substituted with 1 to 5 substituents selected from the group consisting of halogen, hydroxyl, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, and phenylthio; or $R^9$ is a heterocyclic group as defined for $R^1$;

—CO—$OR^6$ as defined above; or

—CO—$NR^7R^8$ as defined above; and $R^4$ is hydrogen or a lower alkyl group; or a salt thereof.

2. A compound according to claim 1, wherein R' is a five- or six-membered nitrogen-containing heterocyclic group.

3. A compound according to claim 1, wherein R' is 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxide of 2-, 3- or 4-pyridyl, 2-, 4- or 5-pyrimidinyl, N-oxide of 2-, 4- or 5-pyrimidinyl, 3- or 4-pyridazinyl, pyrazinyl, N-oxide of 3- or 4-pyridazinyl, benzofuryl, benzothiazolyl, benzoxazolyl, triazinyl, oxotriazinyl, tetrazolo[1,5-b]pyridazinyl, triazolo[4,5-b]pyridazinyl, oxoimidazolyl, dioxotriazinyl, pyrrolidinyl, piperidyl, pyranyl, thiopyranyl, 1,4-oxazinyl, morpholinyl, 1,4-thiazinyl, 1,3-thiazinyl, piperazinyl, benzoimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothia zinyl, or phenoxazinyl.

4. A compound according to claim 2, wherein the heterocyclic group is substituted with 1 to 5 substituents selected from the group consisting of $C_{1-15}$ alkyl; $C_{3-10}$ cycloalkyl; $C_{2-10}$ alkenyl; $C_{2-11}$ alkynyl; $C_{3-10}$ cycloalkenyl; $C_{6-10}$ aryl; $C_{7-10}$ aralkyl; nitro; hydroxyl; mercapto; oxo; thioxo; cyano; carbamoyl; carboxyl; $C_{1-4}$ alkoxycarbonyl; sulfo; halogens; $C_{1-4}$ alkoxy; $C_{8-10}$ aryloxy; $C_{1-4}$ alkylthio; $C_{6-10}$ arylthio; $C_{1-4}$ alkylsulfinyl; $C_{6-10}$ arylsulfinyl; $C_{1-4}$ alkylsulfonyl; $C_{6-10}$ arylsulfonyl; amino; $C_{2-6}$ acylamino; mono- or di-$C_{1-4}$ alkylamino; $C_{6-10}$ arylamino; $C_{2-4}$ acyl; $C_{6-10}$ arylcarbonyl; 2- or 3thienyl; 2- or 3-furyl; 3-, 4- or 5-pyrazolyl; 2-, 4- or 5thiazolyl; 3-, 4- or 5-isothiazolyl; 2-, 4- or 5-oxazolyl; 3-,4- or 5-isoxazolyl; 2-, 4- or 5-imidazolyl; 1,2,3- or 1,2,4-triazolyl; ]H- or 2H-tetrazolyl; 2-, 3- or 4-pyridyl; 2-, 4-or 5-pyrimidinyl; 3- or 4-pyridazinyl; quinolyl; isoquinolyl; and indolyl.

5. A compound according to claim 4, wherein $R^1$ is 2-, 3or 4-pyridyl or 2-, 4- or 5-thiazolyl, which is substituted with 1 to 4 halogens.

6. A compound according to claim wherein the $C_{1-15}$ alkyl, $C_{2-10}$ alkenyl, $C_{2-10}$ alkynyl, $C_{1-4}$ alkoxy, $C_{1-4}$ alkylthio, $C_{1-4}$ alkylsulfinyl, $C_{1-4}$ alkylsulfonyl, amino, mono- or di-$C_{1-4}$ alkylamino, $C_{3-6}$ cycloalkylamino, and $C_{6-10}$ arylamino are each independently substituted with one to five substituent groups selected from the group consisting of halogen; hydroxyl; $C_{1-4}$ alkoxy; and $C_{1-4}$ alkylthio.

7. A compound according to claim 1, wherein $R^3$ is a $C_{1-15}$ alkyl, $C_{3-10}$ to cycloalkyl $C_{2-10}$ alkenyl, $C_{2-10}$ alkynyl, or $C_{3-10}$ cycloalkenyl group.

8. A compound according to claim 1, wherein $R^3$ is cyano, —CO—$R^9$ wherein $R^9$ is hydrogen, a substituted or unsubstituted hydrocarbon group or a substituted or unsubstituted heterocyclic group, or —CO—$OR^{10}$ wherein $R^{10}$ is a substituted or unsubstituted hydrocarbon group or a substituted or unsubstituted heterocyclic group, or —CO—$NR^{11}R^{12}$ wherein $R^{11}$ and $R^{12}$ which are the same or different, are each independently hydrogen, a substituted or unsubstituted hydrocarbon group or a substituted or unsubstituted heterocyclic group, or $R^{11}$ and $R^{12}$, taken together with the nitrogen atom to which they are attached are a cyclic amino group.

9. A compound according to claim 1, wherein $R^3$ is —CO—$R^9$ wherein $R^9$ is a substituted or unsubstituted hydrocarbon group or a substituted or unsubstituted heterocyclic group.

10. A compound according to claim 9, wherein $R^9$ is a $C_{1-5}$ alkyl, $C_{3-10}$ cycloalkyl, $C_{2-10}$ alkenyl, $C_{2-10}$ alkynyl, or $C_{3-10}$ cycloalkenyl group.

11. A compound according to claim 1, wherein $R^3$ is —CO—$OR^{10}$ wherein $R^{10}$ is a substituted or unsubstituted hydrocarbon group or a substituted or unsubstituted heterocyclic group.

12. A compound according to claim 11, wherein $R^{10}$ is $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl group.

13. A compound according to claim 1, wherein $R^3$ is hydrogen; $C_{1-4}$ alkyl; $C_{1-7}$ acyl; $C_7$-$C_{12}$ arylcarbonyl; $C_{2-7}$ alkoxycarbonyl; $C_7$-$C_{12}$ aryloxycarbonyl; $C_8$-$C_{13}$ aralkyloxycarbonyl; $C_{2-7}$ alkylaminocarbonyl; di-$C_{1-4}$ alkylaminocarbonyl; saturated cyclic aminocarbonyl; or $C_{1-4}$ alkylsulfonyl.

14. A compound according to claim 1, wherein $R^1$ is —CO—$OR^6$ wherein $R^6$ is a substituted or unsubstituted hydrocarbon group or a substituted or unsubstituted heterocyclic group.

15. A compound according to claim 14, wherein $R^6$ is $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl group.

16. A compound according to claim 1, wherein $R^2$ is $C_{2-7}$ alkoxycarbonyl.

17. A compound according to claim 1, wherein $R^4$ is $C_{1-4}$ alkyl.

18. A compound of the formula:

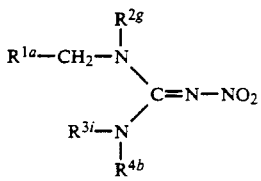

[$I^m$]

wherein $R^{1a}$ is pyridyl, halogenopyridyl, thiazolyl, or halogenothiazolyl; $R^{2s}$ is $C_{2-7}$ alkoxycarbonyl, $C_7$–$C_{12}$ aryloxycarbonyl, $C_8$-$C_{13}$ aralkyloxycarbonyl, $C_7$-$C_{12}$ aryloxythiocarbonyl, $C_{2-7}$ alkylaminocarbonyl, di-$C_{1-4}$ alkylaminocarbonyl, alicyclic aminocarbonyl, or $C_{1-4}$ alkylsulfonyl; $R^{3i}$ is hydrogen, $C_{1-4}$ alkyl, $C_{7-12}$ arylcarbonyl, $C_7$-$C_{12}$ aryloxycarbonyl $C_8$-$C_{13}$ aralkyloxycarbonyl, $C_{2-7}$ alkylaminocarbonyl, di-$C_{1-4}$ alkylaminocarbonyl, alicyclic aminocarbonyl, or $C_{1-4}$ alkylsulfonyl; and $R^{6b}$ is hydrogen or $C_{1-4}$ alkyl; or a salt thereof.

19. A compound according to claim 18, wherein $R^{1a}$ is halogenopyridyl or halogenothiazolyl.

20. A compound according to claim 1 of the formula:

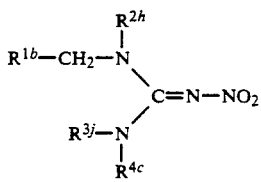

[$I^n$]

wherein $R^{1b}$ is pyridyl, halogenopyridyl, thiazolyl, or halogenothiazolyl; $R^{2b}$ is $C_{2-7}$ alkoxycarbonyl; $R^{3j}$ is hydrogen; and $R^{4b}$ is methyl or ethyl; or a salt thereof.

21. A compound according to claim 18, which is 1-(2-chloro-5-thiazolylmethyl)-1-cyano-3,3-dimethyl-2-nitroguanidine or a salt thereof.

22. A compound according to claim 18, which is 1-(2-chloro-5-thiazolylmethyl)-1,3-diphenoxycarbonyl-3-methyl-2-nitroguanidine or a salt thereof.

23. A compound according to claim 18, which is 1-(2-chloro-5-thiazolylmethyl)- 1-dimethylaminocarbonyl-3-methyl-2-nitroguanidine or a salt thereof.

24. A compound according to claim 18, which is 1-(2-chloro-5-thiazolylmethyl)-3-methyl-1-morpholinocarbonyl-2-nitroguanidine or a salt thereof.

25. A compound according to claim 18, which is 1-(2-chloro-5-thiazolylmethyl)-3,3-dimethyl-1-methanesulphonyl-2-nitroguanidine or a salt thereof.

26. A compound according to claim 18, which is 1-(2-chloro-5-thiazolylmethyl)-3,3-dimethyl-2-nitro-1-phenoxythiocarbonylguanidine or a salt thereof.

27. A compound according to claim 18, which is 1-(2-chloro-5-thiazolylmethyl)-1-methoxycarbonyl-3-methyl-2-nitroguanidine or a salt thereof.

28. A compound according to claim 18, which is 1-(t-butoxycarbonyl)-1-(2-chloro-5-thiazolylmethyl)-3-methyl-2-nitroguanidine or a salt thereof.

29. A compound according to claim 18, which is 1-(2-chloro-5-thiazolylmethyl)-1-ethoxycarbonyl-3-methyl-2-nitroguanidine or a salt thereof.

30. A compound according to claim 18, which is 1-(2-chloro-5-thiazolylmethyl)-1-n-propoxycarbonyl-3-methyl-2-nitroguanidine or a salt thereof.

31. A compound according to claim 18, which is 1-(2-chloro-5-thiazolylmethyl)-1-isopropoxycarbonyl-3-methyl-2-nitroguanidine or a salt thereof.

32. A compound according to claim 18, which is 1-(n-butoxycarbonyl)-1-(2-chloro-5-thiazolylmethyl)-3-methyl-2-nitroguanidine or a salt thereof.

33. A compound according to claim 18, which is 1-(isobutoxycarbonyl)-1-(2-chloro-5-thiazolylmethyl)-3-methyl-2-nitroguanidine or a salt thereof.

34. A compound according to claim 18, which is 1-(2-chloro-5-thiazolylmethyl)-1-(1-chloroethoxycarbonyl)-3-methyl-2-nitroguanidene or a salt thereof.

35. A compound according to claim 18, which is 1-(2-chloro-5-thiazolylmethyl)-3-methyl-1-pyrrolidinocarbonyl-2-nitroguanidine or a salt thereof.

36. A compound according to claim 18, which is 1(2-chloro-5-thiazolylmethyl)-3-methyl-1-benzyloxycarbonyl-2-nitroguanidine or a salt thereof.

37. A pesticidal composition comprising an effective amount of a substituted nitroguanidine compound of the formula:

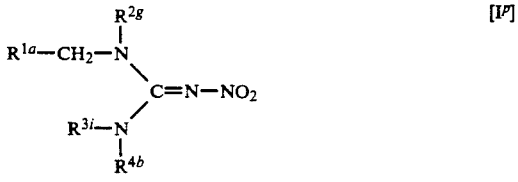

[$I^p$]

wherein $R^{1a}$ is pyridyl, halogenopyridyl, thiazolyl, or halogenothiazolyl; $R^{2g}$ is $C_{2-7}$ alkoxycarbonyl, $C_7$-$C_{12}$, $C_8$-$C_{13}$ aralkyloxycarbonyl, $C_7$-$C_{12}$ aryloxythiocarbonyl, $C_{2-7}$ alkylaminocarbonyl, di-$C_{1-4}$ alkylaminocarbonyl, alicyclic aminocarbonyl, or $C_{1-4}$ alkylsulfonyl; $R^{3l}$ is hydrogen, $C_{1-4}$ alkyl, $C_{7-12}$ arylcarbonyl, $C_2$-$C_{12}$ aryloxycarbony, $C_8$-$C_{13}$ aralkyloxycarbonyl, $C_{2-7}$ alkylaminocarbonyl, di-$C_{1-4}$ alkylaminocarbonyl, alicyclic aminocarbonyl, or $C_{1-4}$ alkylsulfonyl; and $R^{4b}$ is hydrogen or $C_{1-4}$ alkyl; or a salt thereof, in admixture with an acceptable carrier, vehicle, diluent or excipient.

38. A pesticidal composition comprising an effective amount of a substituted nitroguanidine compound according to claim 19 or a salt thereof in admixture with an acceptable carrier, vehicle, diluent or excipient.

39. A method for controlling a pest which comprises applying an effective amount of the substituted nitroguanidine compound of the formula [I] according to claim 1 or a salt thereof to prevent said pest.

40. A compound according to claim 1, wherein $R^3$ is selected from the group consisting of hydrogen and a hydrocarbon group except for one substituted with an oxo group at the binding site as defined in claim 1.

41. A compound according to claim 1, wherein $R^3$ is hydrogen and $R^4$ is lower alkyl.

42. A pesticidal composition comprising an effective amount of a compound according to claim 1 in admixture with an acceptable carrier, vehicle, diluent or excipient.

* * * * *